US010175251B2

(12) United States Patent
Grus et al.

(10) Patent No.: US 10,175,251 B2
(45) Date of Patent: Jan. 8, 2019

(54) DIAGNOSTIC METHODS FOR GLAUCOMA

(75) Inventors: Franz Grus, Vreden (DE); Nils Boehm, Ingelheim (DE); Norbert Pfeiffer, Mainz (DE)

(73) Assignee: M-LAB GMBH, Mainz (DE)

(*) Notice: Subject to any disclaimer, the term of this patent is extended or adjusted under 35 U.S.C. 154(b) by 1131 days.

(21) Appl. No.: 13/641,009

(22) PCT Filed: Apr. 13, 2011

(86) PCT No.: PCT/CH2011/000077
§ 371 (c)(1),
(2), (4) Date: Mar. 20, 2013

(87) PCT Pub. No.: WO2011/127616
PCT Pub. Date: Oct. 20, 2011

(65) Prior Publication Data
US 2013/0172204 A1 Jul. 4, 2013

Related U.S. Application Data

(60) Provisional application No. 61/342,363, filed on Apr. 13, 2010.

(51) Int. Cl.
*G01N 33/564* (2006.01)
*C12Q 1/68* (2018.01)
*G01N 33/68* (2006.01)

(52) U.S. Cl.
CPC ... *G01N 33/6893* (2013.01); *G01N 2800/168* (2013.01)

(58) Field of Classification Search
None
See application file for complete search history.

(56) References Cited

U.S. PATENT DOCUMENTS 6,399,398 B1 6/2002 Cunningham et al.
7,442,720 B2 10/2008 Chan et al.
(Continued)

FOREIGN PATENT DOCUMENTS

EP 1832600 A1 9/2007
EP 2354792 A1 8/2011
(Continued)

OTHER PUBLICATIONS

Grus et al., Complex autoantibody repertoires in patients with glaucoma. Mol Vis. Feb. 25, 2004;10:132-7.*
(Continued)

*Primary Examiner* — Adam Weidner
*Assistant Examiner* — Aurora M Fontainhas
(74) *Attorney, Agent, or Firm* — Larson & Anderson, LLC

(57) ABSTRACT

The invention concerns a first diagnostic method for glaucoma based on an analysis of autoimmune reactivity in body fluids against at least one sample of at least partially purified ocular antigens, wherein the autoimmune reactivity against individual antigens is measured and transformed into a glaucoma score to determine the diagnostic result. Further aspects of the invention include antigen carrying elements carrying at least one sample of the at least partially purified ocular antigens and kits for diagnosis of glaucoma. Further aspects include methods of collecting a body fluid such as tears for the use in the diagnostic method for glaucoma. Yet further aspects include ocular antigens serving as diagnostic markers and/or for preparing pharmaceutical compositions for treatment of glaucoma. The invention further concerns a second diagnostic method for glaucoma comprising the steps of a) providing an in vitro culture of cells; b) incubating a body fluid from a test individual with the in vitro culture of cells or incubating components, which are frac- (Continued)

tionated from the body fluid or from a body specimen of the test individual with the in vitro culture of cells; c) analyzing protein expression of the cells and/or analyzing the viability of the cells after treatment according to step b); and d) comparing the results of the analysis in step c) with standard data to determine a diagnostic result.

22 Claims, 17 Drawing Sheets

(56) References Cited

U.S. PATENT DOCUMENTS

| | | | |
|---|---|---|---|
| 2002/0102581 A1* | 8/2002 | Hageman | C12Q 1/6883 435/6.12 |
| 2003/0017501 A1* | 1/2003 | Hageman | C12Q 1/6883 435/7.1 |
| 2003/0149997 A1 | 8/2003 | Hageman | |
| 2006/0166268 A1* | 7/2006 | Grus | G01N 33/564 435/7.1 |
| 2006/0263819 A1* | 11/2006 | Hageman | C12Q 1/6883 435/6.12 |
| 2010/0010375 A1 | 1/2010 | Haar et al. | |
| 2010/0093108 A1 | 4/2010 | Khattar et al. | |
| 2011/0182908 A1 | 7/2011 | Hageman et al. | |

FOREIGN PATENT DOCUMENTS

| | | |
|---|---|---|
| KR | 20100087275 A | 8/2010 |
| KR | 20100087276 A | 8/2010 |
| RU | 2187983 C2 | 8/2002 |
| RU | 2314535 C1 | 1/2008 |
| RU | 2371721 C2 | 10/2009 |
| WO | 2004/036220 A1 | 4/2004 |
| WO | 2009/145478 A2 | 12/2009 |

OTHER PUBLICATIONS

Albumin, Sigma Aldrige catalogue Oct. 9, 1996 http://www.sigmaaldrich.com/content/dam/sigma-aldrich/docs/Sigma/Product_Information_Sheet/a1887pis.pdf Downloaded Mar. 11, 2016.*

Boehm et al., ARVO annual meeting abstract, Apr. 2009.*

Joachim et al., Sera of glaucoma patients show autoantibodies against myelin basic protein and complex autoantibody profiles against human optic nerve antigens. Graefes Arch Clin Exp Ophthalmol (2008) 246:573-580.*

Kingsmore, Multiplexed protein measurement: technologies and applications of protein and antibody arrays. Nature Reviews Drug Discovery | AOP, published online Mar. 17, 2006; doi:10.1038/nrd2006 (Year: 2006).*

Joachim et al., IgG antibody patterns in aqueous humor of patients with primary open angle glaucoma and pseudoexfoliation glaucoma. Molecular Vision 2007; 13:1573-9 (Year: 2007).*

Borazan, M. et al. "Aqueous Humor and Plasma Levels of Vascular Endothelial Growth Factor and Nitric Oxide in Patients with Pseudoexfoliation Syndrome and Pseudoexfoliation Glaucoma", J. Glaucoma, 2010, pp. 207-211, vol. 19, No. 3.

Crisanti, P. et al. "The role of PKCζ in NMDA-induced retinal ganglion cell death: Prevention by aspirin", Apoptosis, 2006, pp. 983-991, vol. 11, No. 6.

Carter-Dawson, L. et al. "Elevated Albumin in Retinas of Monkeys with Experimental Glaucoma", Investigative Ophthalmology & Visual Science, Feb. 2010, pp. 952-959, vol. 51, No. 2.

De La Paz, M. et al. "Effect of Age pn Superoxide Dismutase Activity of Human Trabecular Meshwork", Investigative Ophthalmology & Visual Science, Aug. 1996, pp. 1849-1853, vol. 37, No. 9.

Duan, X. et al. "Proteomic analysis of aqueous humor from patients with primary open angle glaucoma", Molecular Vision, 2010, pp. 2839-2846, vol. 16.

Ferreira, S. et al. "Oxidative Stress Markers in Aqueous Humor of Glaucoma Patients", Am. J. Ophthalmology, 2004, pp. 62-69, vol. 137.

Ghaffariyeh, A. et al. "Brain-derived neurotrophic factor in patients with normal-tension glaucoma", Optometry, 2009, pp. 635-638, vol. 80.

Grus, F. et al. "Transthyretin and complex protein pattern in aqueous humor of patients with primary open-angle glaucoma", Molecular Vision, 2008, pp. 1437-1445, vol. 14.

Guan, Y. et al. "Retinal ganglion cell damage induced by spontaneous autoimmune optic neuritis in MOG-specific TCR transgenic mice", Journal of Neuroimmunology, 2006, pp. 40-48, vol. 178.

Hu, D. et al. "Vascular Endothelial Growth Factor is Increased in Aqueous Humor of Glaucomatous Eyes", Journal of Glaucoma, 2002, pp. 406-410, vol. 11.

Khurana, R. et al. "The role of protein kinase C in modulation of aqueous humor outflow facility", Experimental Eye Research, 2003, pp. 39-47, vol. 76.

Ko, M. et al. "Patterns of retinal ganglion cell survival after brain-derived neurotrophic factor administration in hypertensive eyes of rats", Neuroscienec Letters, 2001, pp. 139-142, vol. 305.

Kremmer, S. et al. "Antiohosphatidylserine antibodies are elevated in normal tension glaucoma", Clin. Exp. Immunol., 2001, pp. 211-215, vol. 125.

Pasutto, F. et al. "Heterozygous NTF4 Mutations Impairing Neurotrophin-4 Signaling in Patients with Primary Open-Angle Glaucoma", The American Journal of Human Genetic, Oct. 2009, pp. 447-456, vol. 85.

Rudzinski, M. et al. "Antiangiogenic Characteristics if Astrocytes from Optic Nerve Heads with Primary Open-angle Glaucoma", Arch Ophthalmology, May 2008, pp. 679-685, vol. 126, No. 5.

Schori, H. et al. "Vaccination for protection of retinal ganglion cells against death from glutamate cytotoxicity and ocular hypertension: Implications for glaucoma", PNAS, Mar. 2001, pp. 3398-3403, vol. 98, No. 6.

Tripathi, R. et al. "Quantitative and Qualitative Analyses of Transferrin in Aqueous Humor From Patients with Primary and Secondary Glaucomas", Investigative Ophthalmology & Visual Science, Sep. 1992, pp. 2866-2873, vol. 33, No. 10.

Vesaluoma, M. et al. "Cellular and Plasma fibronectin in the aqueous humour of primary open-angle glaucoma, exfoliative glaucoma and cataract patients", Eye, 1998, pp. 886-890, vol. 12.

Agar, A et al., Retinal ganglion cell line apoptosis induced by hydrostatic pressure, Brain Research, 2006, pp. 191-200, vol. 1086, No. 1, Publisher: Elsevier.

Cancino-Diaz, M. E. et al., Amino acid regions 357-368 and 418-427 of *Streptococcus pyogenes* 60 kDa heat shock protein are recognized by antibodies from glaucomatous patient sera, Microbial Pathogenesis, 2010, pp. 239-244, vol. 48, Publisher: Elsevier.

Grus, F. H., Relationship between Oxidative Stress and Autoimmunity in Glaucoma, Clinische Monatsblatter fur Augenheilkunde, 2010, pp. 114-119, vol. 227, No. 2.

Ikeda Y. et al., Two Cases of Primary Open Angle Glaucoma with Serum Autoantibody Against Retinal Ganglion Cells, Jpn J. Ophthalmol, 2000, pp. 648-652, vol. 44, Publisher: Elsevier Science Inc.

Joachim, S. C. et al, Autoantibodies in Patients with Glaucoma: A Comparison of IgG Serum Antibodies against Retinal, Optic Nerve, and Optic Nerve Head Antigen, Invest Ophthalmol Vis Sci., 2003, p. E-Abstract 4358, vol. 44.

Joachim, S. C. et al., Antibodies to aB-Crystallin, Vimentin, and Heat Shock Protein 70 in Aqueous Humor of Patients with Normal Tension Glaucoma and IgG Antibody Patterns Against Retinal Antigen in Aqueous Humor, Current Eye Research, 2007, pp. 501-509, vol. 32.

Maruyama, I. et al., Retinal Ganglion Cells Recognized by Serum Autoantibody against y-Enolase Found in Glaucoma Patients, Investigative Ophthalmology & Visual Science, 2000, pp. 1657-1665, vol. 41, No. 7.

Morohoshi, K. et al., Autoimmunity in retinal degeneration: Autoimmune retinopathy and age-related macular degeneration, Journal of Autoimmunity, 2009, pp. 247-254, vol. 33, Publisher: Elsevier.

(56) References Cited

OTHER PUBLICATIONS

Romano, C. et al., Anti-Rhodopsin Antibodies in Sera From Patients with Normal-Pressure Glaucoma, Investigative Ophthalmology & Visual Science, 1995, pp. 1968-1975, vol. 36, No. 10.

Tezel, G. et al., Autoantibodies to Small Heat Shock Proteins in Glaucoma, Investigative Ophthalmology & Visual Science, 1998, pp. 2277-2287, vol. 39, No. 12.

Tong, M. G. et al., Immunoproteomic Analysis of Serum Antibody Complexes in Glaucoma Patients, Invest Ophthalmol Vis Sci., 2011, p. E-Abstract 2431, vol. 52.

Agarwal, N. et al. "Comparison of expression profile of neurotrophins and their receptors in primary and transformed rat retinal ganglion cells" Molecular Vision, 2007, pp. 1311-1318, vol. 13.

Grus, F. H. et al. "Transthyretin and complex protein pattern in aqueous humor of patients with primary open-angle glaucoma" Molecular Vision, 2008, pp. 1437-1445, vol. 14.

Ikeda, Y. et al. "Clinical significance of serum antibody against neuron-specific enolase in glaucoma patients" Jpn J. Ophthalmol, 2002, pp. 13-17, vol. 46, No. 1.

Joachim, SC. et al. "Sera of glaucoma patients show autoantibodies against myelin basic protein and complex autoantibody profiles against human optic nerve antigens" Graefes Arch Clin Exp Ophthalmol., 2008, pp. 573-580, vol. 246, No. 4, Abstract only.

Savagian, C. et al. "Comparison of the distribution of glial fibrillary acidic protein, heat shock protein 60, and hypoxia-inducible factor-1a in retinas from glaucomatous and normal canine eyes" American Journal of Veterinary Research, 2008, pp. 265-272, vol. 69, No. 2, Abstract only.

Wax, MB. et al. "Serum autoantibodies to heat shock proteins in glaucoma patients from Japan and the United States", Ophthalmology, 2001, pp. 296-302, vol. 108, No. 2, Abstract only.

Gao, H. et al. "Up-regulation of Brain-Derived Neurotrophic Factor Expression by Brimonidine in Rat Retinal Ganglion Cells", Arch Ophthalmology, Jun. 2002, pp. 797-803, vol. 120.

McLaren, N. et al. "Evaluation of the β2-Adrenergic Receptor Gene as a Candidate Glaucoma Gene in 2 Ancestral Populations", Arch Ophthalmology, Jan. 2007, pp. 105-111, vol. 125.

Grus, et al, Autoantibody Profiles in Tear Fluid as a Diagnostics Tool in Glaucoma, ARVO Annual Meeting Abstract, Apr. 2010, 2 pages, Retrieved from URL: http://iovs.arvojournals.org/article.aspx?articleid=2374712.

Bohm, et al., Proteing Micro-Arrays as an Effective Method for Antibody Profiling in Glaucoma, ARVO Annual Meeting Abstract, May 2008, 2 pages.

Seigel, G. M. et al., Expression of Glial Markers in a Retinal Precursor Cell Line, Mol Vis, 1996, 7 pages, vol. 2.

Van Bergen, N. J., et al., Recharacterization of the RGC-5 Retinal Ganglion Cell Line, Investigative Ophthalmology & Visual Science, 2009, pp. 4267-4272, vol. 50, No. 9.

Lowry, O. H. et al., Protein Measurement with the Foling Phenol Reagent*, Department of Pharmacology, Washington University School of Medicine, St. Louis, MO, 1951, pp. 265-275.

Litvinenko, V.I. et al. "Computer System for Solving the Classification Problems on the Basis of the Modified Immune Algorithms" 2008, pp. 1-9, vol. 2, No. 22 (including translation).

* cited by examiner

Figure 2 A and Figure 2 B:
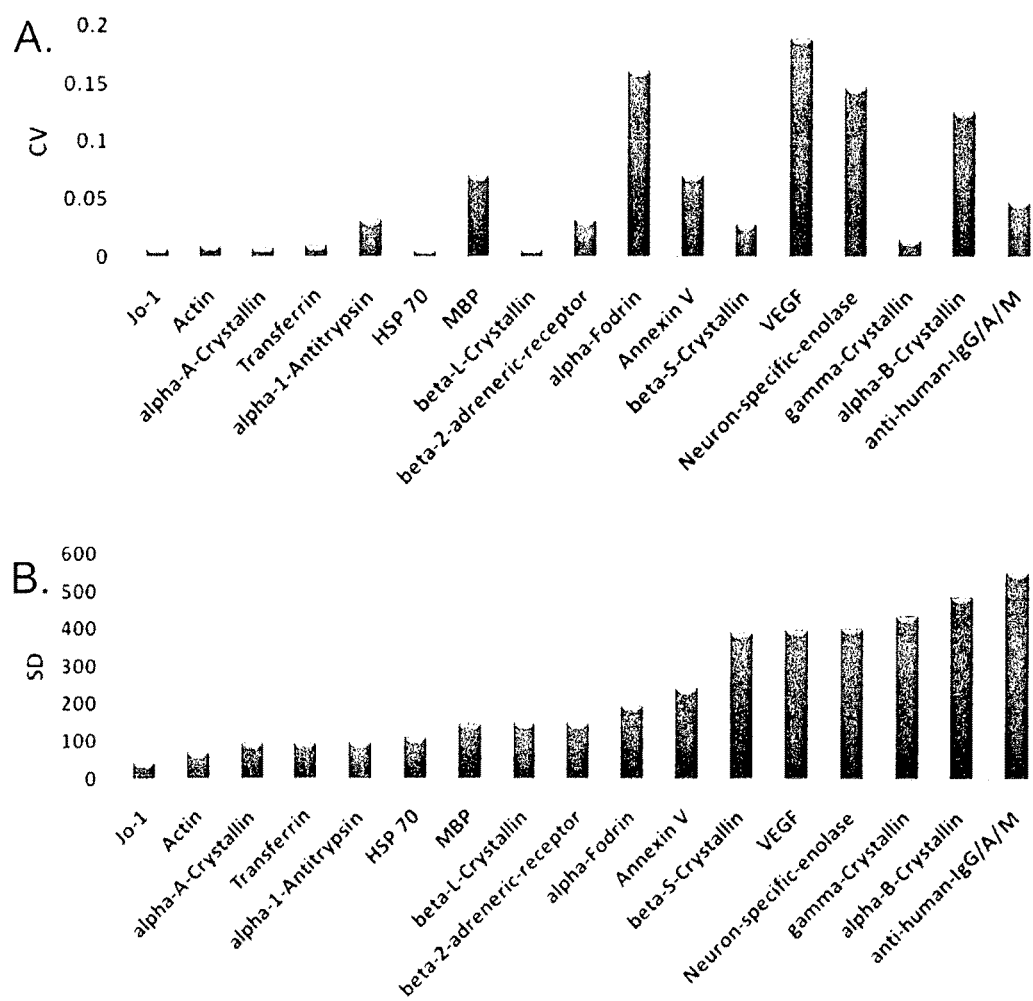

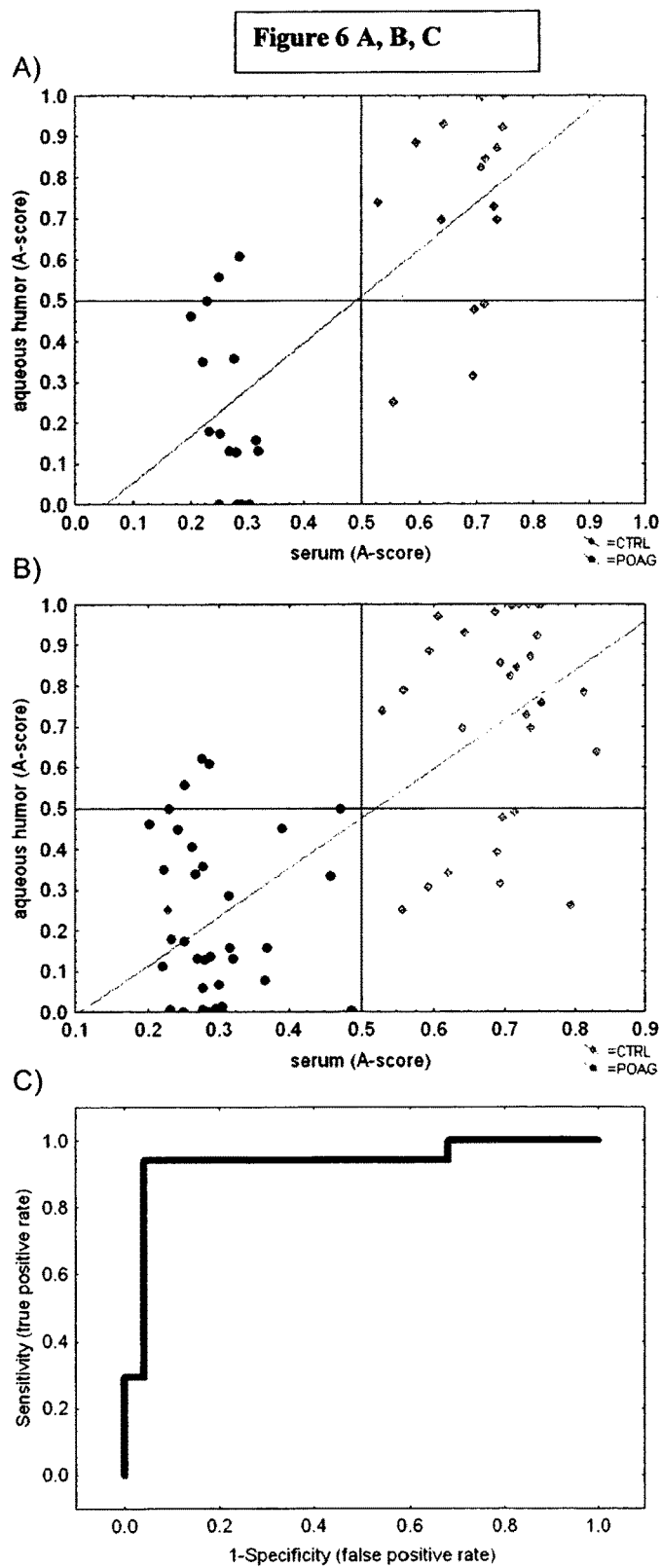

Figure 14 a, b:
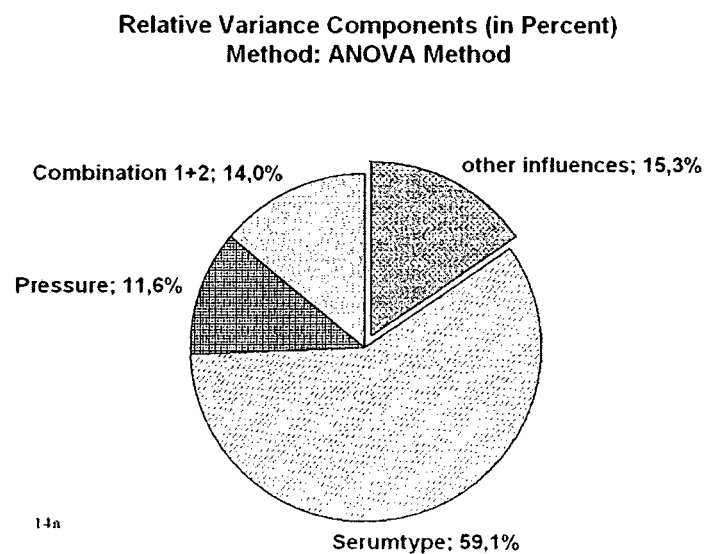
14a
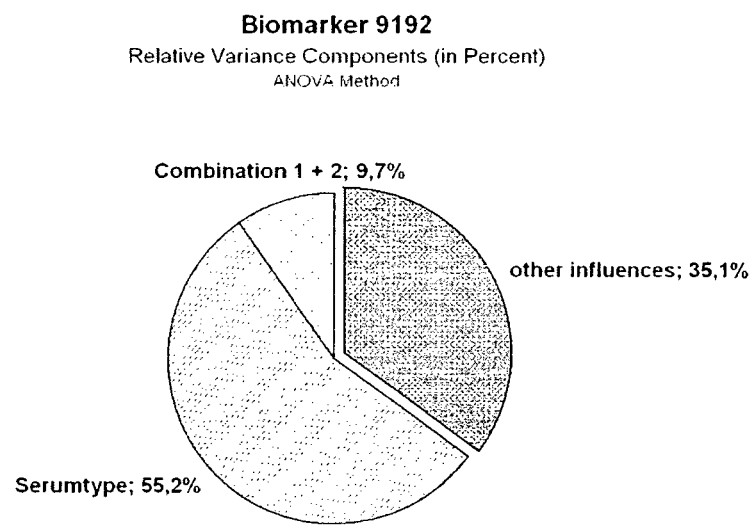
14b

Figure 15a, b:
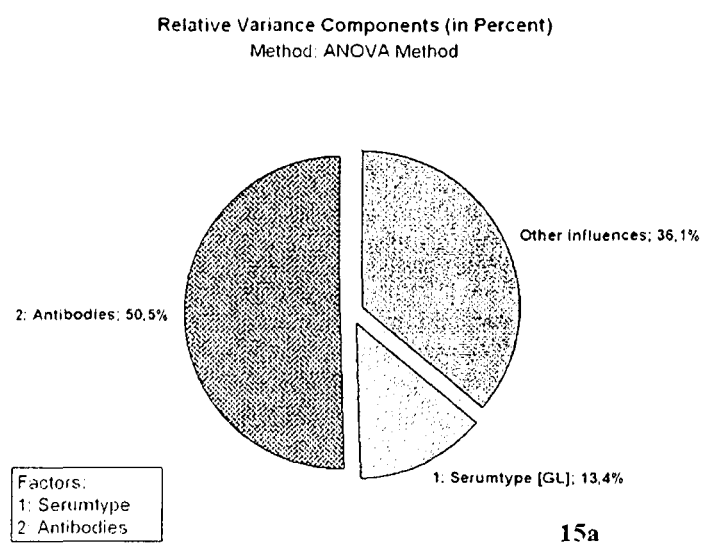
15a
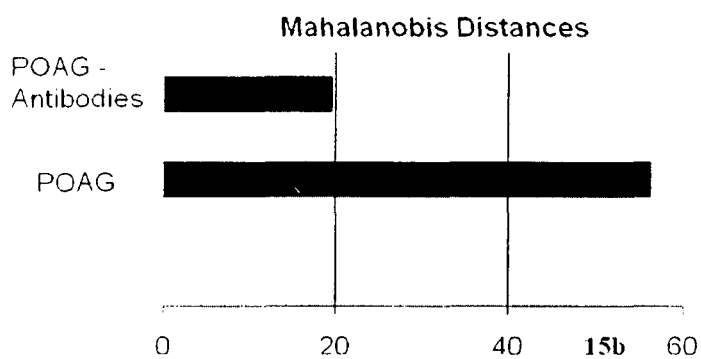
15b

Figure 16a, b:
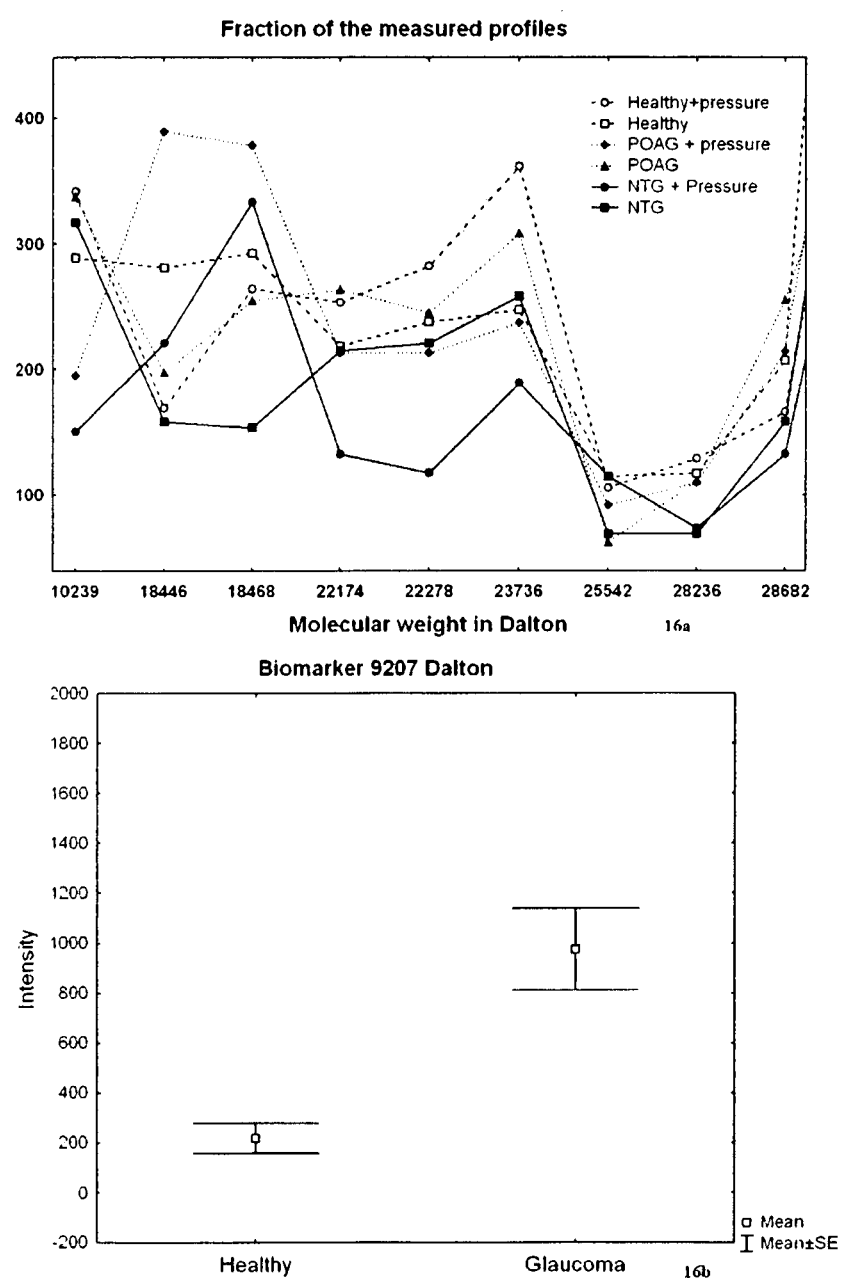

☆ p< 0.01

★ p< 0.05

★ p< 0.05

DIAGNOSTIC METHODS FOR GLAUCOMA

FIELD OF THE INVENTION

The invention lies in the field of medical diagnostics and relates in particular to methods of diagnosing glaucoma based on analysis of autoimmune reactivity. This invention comprises two diagnostic methods for glaucoma. Both the first and the second diagnostic method rely on the autoimmune reactivities in body fluids of glaucoma patients. A further aspect of the invention relates to therapeutic methods modulating the autoimmune reactivity of glaucoma patients.

A first diagnostic method for glaucoma is based on an analysis of autoimmune reactivity of bodily fluids against ocular antigens which are at least partially purified. A second diagnostic method for glaucoma is based on the analysis of the effect of autoantibodies in body fluids, on the protein expression of in vitro cultured retinal ganglion cells (RGC).

BACKGROUND OF THE INVENTION

Glaucoma is a group of ocular disorders characterized by progressive loss of retinal ganglion cells and their axons, and a gradual loss of visual field. It is one of the leading causes of blindness worldwide. Glaucoma has a prevalence of about 1-2% in the general population in Europe. Up to 3-4% of people aged over 60 are affected by the disease. The most common form of glaucoma is the primary open-angle glaucoma (POAG), with a prevalence ranging from 1.1% to 2%.

The pathogenesis of glaucoma is only partly understood and an elevated intraocular pressure is not solely responsible for the disease. An increased intraocular pressure is still considered as a major risk factor, but other pathogenic factors, such as apoptotic processes, elevated nitric oxide levels or an involvement of the immune system are likely to be relevant.

Furthermore, an elevated intraocular pressure is quite prevalent (10% of the population at age 40), however, only some of these develop glaucoma over the years. So far there are no standard diagnostic tests to identify which persons with an elevated intraocular pressure develop glaucoma. Since an early treatment of glaucoma is crucial to prevent loss of vision, there is a need for improved diagnostic tools, which detect glaucoma at an early stage independent of an elevated intraocular pressure.

An elevated intraocular pressure is known as a major cause for retinal cell death and the development of the glaucoma disease. Elevated pressure as a cause for cell death has been reproduced in vitro. Agar et al. (Brain Res. 2006. 1086 (1): p. 191-200) exposed in vitro cultures of retinal ganglion cell lines to elevated hydrostatic pressure and induced cell death.

However, it is also known that about 30% of the glaucoma cases are not accompanied by an elevated intraocular pressure. At least some forms of the Glaucoma disease fit the pattern of neurodegenerative diseases with progressive dysfunction of aspects of the nervous system along with progressive atrophy of the affected structures of the peripheral or central nervous system. Therefore, further causes and mechanisms are discussed, which besides an elevated intraocular pressure are leading to the destruction of retinal ganglion cells such as for example an elevated nitric oxide level or a T-cell mediated process or autoimmune attacks.

Early detection methods for Glaucoma are still limited. Measuring the intraocular pressure can detect some of the patients but fluctuant pressure levels can also give a false negative result. At the time, when patients themselves recognize a loss of visual function, a large irreversible defect of retinal ganglion cells has in most cases already occurred.

The roughly 30% of the glaucoma cases which are not accompanied by an elevated intraocular pressure are termed as normal tension glaucoma. The traditional detection method measuring an elevated intraocular pressure fails with these patients. Considering the lack of a diagnostic method for normal tension glaucoma as well as the lack of a detection method for early stage glaucoma, it is necessary to develop methods for detecting glaucoma independent of the intraocular pressure. Autoimmunity as an important factor in Glaucoma has been demonstrated by several studies showing serum antibodies against ocular antigens. For example, heat shock proteins HSP27, HSP60, $\alpha$-B-crystallin, $\gamma$-enolase, $\alpha$-fodrin, gluthathione-S-transferase, and glycosaminoglycans, have different levels of binding reactivities in glaucoma patients compared to healthy subjects (e.g. Joachim, S. C., et al., Curr. Eye Res. 2007, 32 (6): p. 501-9.) Interestingly, not only elevated antibody reactivities, which might have an autoagressive impact, but for certain antigens diminished autoimmune reactivities are characteristic in bodyfluids of glaucoma patients. Furthermore, it could be shown that the direct application of anti-HSP antibodies results in an apoptosis of retinal ganglion cells in a cell culture approach (Tezel G, et al. Invest Ophthalmol. Vis. Sci. 1998; 39:2277-2287).

Previously, diagnostic methods based on the specific autoimmune reactivity pattern of glaucoma patients were disclosed. For example, WO2004/036220 discloses methods for diagnosis of glaucoma by the analysis of the complex autoantibody repertoire in body fluids such as serum, tears, aqueous humor or saliva against ocular antigens. As source for ocular antigens crude mixtures of retinal antigens, optic nerve antigens and others have been used and the complex autoimmune reactivity patterns have been measured. A variety of analytical immunological techniques including Western blot assays, chemiluminescence assay, ELISA, Radioimmunoassays for detection and measurement of the autoimmune reactivity patterns as well as methods for digital image detection, processing and analysis were used for the generation and comparative analysis of the autoimmune reactivity patterns of test individuals, healthy individuals and glaucoma patients were disclosed. The WO2004/036220 document teaches diagnostic methods for glaucoma relying on the autoimmune reactivity patterns against ocular antigens, which are not isolated from complex mixtures of a large number of ocular antigens and most of which have not been identified. The difference of the autoimmune reactivity patterns in body fluids from test individuals, healthy individuals and glaucoma patients then yields the diagnostic result. However, studies in the diagnostic field concerning other diseases such as cancer have revealed, that diagnosis based on autoimmune reactivity against biomarkers of unknown identity is often unreliable. Thus there is a need for reliable methods of diagnosis of glaucoma, which are independent of an elevated intraocular pressure.

It is an object of the current invention to provide alternate and improved and reliable diagnostic methods to detect glaucoma independent of an increased intraocular pressure by analysis of body fluids. It is a further object of the invention to provide diagnostic methods to detect glaucoma with selectable degrees of sensitivity and specificity used for both for rapid testing and for professional laboratory testing. Further objects of the invention include the provision of antigen carrying elements and kits for diagnosing glaucoma as well as newly identified ocular antigens serving as biomarkers for diagnosing glaucoma and as blocking agents in the therapeutic treatment of glaucoma.

SUMMARY OF THE INVENTION

One aspect of the invention concerns a first diagnostic method for glaucoma based on an analysis of autoimmune reactivity in a body fluid against at least one sample comprising at least one at least partially purified ocular antigen, wherein the autoimmune reactivities against one or more known ocular antigens are measured and transformed into a glaucoma score for their preferably weighted contribution of the measured autoimmune reactivities to a diagnostic result.

Further aspects of the invention include antigen carrying elements carrying at least one partially purified ocular antigen and methods of preparing these antigen carrying elements, and using them for diagnosis of glaucoma. Further aspects include kits for diagnosis of glaucoma comprising the antigen carrying element, and optionally auxiliary materials. Further aspects include methods of collecting a body fluid such as tears for the use in the diagnostic method for glaucoma. Yet further aspects include ocular antigens serving as biomarkers for diagnosing glaucoma or serving as therapeutic agents in the therapeutic treatment of glaucoma or serving for the preparation of specific antibodies binding such ocular antigen, for use in a diagnostic or therapeutic method or composition.

The first diagnostic method for glaucoma comprises the steps of (a) providing at least one sample comprising at least one at least partially purified ocular antigen, (b) reacting a body fluid with the at least one ocular antigen sample, (c) detecting and/or quantifying the reactions between autoantibodies in the body fluid and the at least one ocular antigen sample of step b to determine an autoimmune reactivity value, d) comparing measured autoimmune reactivity values with standard data obtained from glaucoma patients and/or healthy individuals to determine a glaucoma score for the at least one antigen sample and e) optionally to determine the diagnostic result by evaluation of the at least one glaucoma score.

The term body fluid of human individuals or animals in the context of this application includes but is not limited to serum, tears, saliva, urine, aqueous humor, vitreous body of the eye or cerebrospinal fluid and fractions thereof or a homogenate of tissue specimens of human individuals or animals and fractions thereof. In preferred embodiments of the method for diagnosis of glaucoma blood serum or tears are used.

Ocular antigen refers to any antigen which occurs also in the eye and obviously some of these ocular antigens mentioned below explicitly are ubiquitous. Ocular antigens present in the eye in particular include retinal antigens, optic nerve antigens, optic nerve head antigens, trabecular network antigens, uveal antigens. It is known that the glaucoma relevant antigens are not restricted to proteins present in retinal ganglion cells but include antigens which are characteristic of neighboring cells such as glia cells or components of the cytoskeleton.

Furthermore, for this application, the term ocular antigens—including all of the specifically named ocular antigens mentioned below—applies not only to the physiological, natural forms of the respective proteins but also to post-translationally modified forms and to any other natural or artificial derivatives such as peptides, and forms, which are tagged, cleaved, chemically modified otherwise including combinations of the mentioned modifications.

At least partially purified ocular antigens refer to ocular antigens, which are isolated from the complex mixture of proteins of their physiological environment by at least partial protein purification with standard protein purification techniques. Ocular antigens of available commercial grade purity are also considered as at least partially purified ocular antigens for use in a diagnostic method for glaucoma in the context of this paper. Such partial purification yields at least 70% of one or more desired ocular antigen by weight of total protein, preferably at least 80% more preferably at least 90% and most preferably at least 95%.

The term ocular antigen sample refers to a sample comprising one or more at least partially purified ocular antigens. In preferred embodiments of the method according to the invention the ocular antigen sample comprises only one ocular antigen and glaucoma scores are determined individually for each of the partially purified ocular antigens separately. In further preferred embodiments two or more partially purified ocular antigens are combined into at least one of the ocular antigen samples. For such samples of ocular antigens the measured autoimmune reactivities correspond to the autoimmune reaction against a combination of two or more ocular antigens, which than leads to one glaucoma score. In contrast to antigens not isolated from their physiological environment such as ocular cell lysates, the relative amounts of the components of the antigen combination is controlled. Such a controlled combination of antigens may also lead to a weighting i.e. the effect of a weight factor which modulates the contribution of the measured autoimmune reactivity of certain ocular antigens to the diagnostic result.

In this paper, the terms 'ocular antigens' or 'antigens' are often used interchangeably and instead of the rather long expressions 'at least partially purified ocular antigens' or 'samples of at least partially purified ocular antigens'.

Autoimmune reactivity or interchangeably immunoreactivity and autoantibody reactivity in the context of this paper refer to the binding activity of autoantibodies present in a body fluid to an at least partially purified ocular antigen, which is incubated with the body fluid.

Methods to detect and measure autoimmune reactivity include standard immunological analytical techniques such as Western blot assays, chemiluminescence assay, ELISA, radioimmunoassays, microarrays and others. Antigens are applied and fixed to an antigen carrying element and then incubated with body fluid containing autoantibodies to be detected. Subsequently bound autoantibodies are identified to determine autoimmune reactivties. Methods of identification include e.g. pre-labeling the sample to be analyzed, adding a secondary antibody, which binds to the antigen-bound autoantibodies or to an indirect label, e.g. labeled goat anti-human immunoglobulins etc. Further methods include analysis of addressable elements such as beads, nanoparticles, tags etc. Detection methods may also include methods, which do not require labeling, for example SELDI-TOF-type (surface enhanced laser desorption/ionization in time of flight mass spectrometry), MALDI (matrix assisted laser desorption/ionization mass spectroscopy or other antibody chip techniques.

The first method for diagnosis of glaucoma according to the invention relies on the difference of the average autoimmune reactivity in healthy persons as compared to in glaucoma patients against certain ocular antigens. Thus, certain titers of autoantibodies against certain ocular antigens in a body fluid are used as a diagnostic evidence for the glaucoma disease.

One aspect of the invention concerns newly identified ocular antigens, to which autoantibodies bind differentially in healthy individuals and glaucoma patients and which are useful diagnostic as markers (or biomarkers) for detecting the glaucoma disease and for therapeutic treatment.

In order to extract information from the measured signals of autoimmune reactivities against ocular antigen samples, the measured signals or values of autoimmune reactivity are compared with standard data, in preferred embodiments the comparison of step d) is performed for each ocular antigen sample, separately. In preferred embodiments the standard data include average values for the autoimmune reactivity measured against each ocular antigen sample for both healthy controls and glaucoma patients. In other preferred embodiments the standard data includes average values for the autoimmune reactivity measured against each ocular antigen sample characteristic for certain stages of the disease. Thus, the diagnosis of different stages of the glaucoma disease and also the monitoring of the progression of the glaucoma disease is within the spirit of the method according to the invention. In further preferred embodiments, the standard data of autoimmune reactivities includes autoimmune reactivities characteristic of subtypes of specific forms of the glaucoma disease.

Such standard data may either be generated by control reactions of the steps (a)-(c) of the method for diagnosis of glaucoma of body fluids from healthy individuals and glaucoma patients which are conducted in parallel with the test samples or such standard data may stem from stored data from control reactions performed under identical conditions at a different time.

In preferred embodiments, the glaucoma score is deducted for each ocular antigen sample from the measured autoimmune reactivity value by correlating the measured value of a test individual to the standard data and transform the measured autoimmune reactivity value into a glaucoma score. In a simplified example a glaucoma score is determined from the autoimmune reactivity measured for each individual ocular antigen sample on an exemplary glaucoma diagnosis scale from 0 to 100, where 0 corresponds to the average value of measured autoimmune reactivity against a particular ocular antigen in healthy persons and 100 corresponds to the average value of measured autoimmune reactivity against this antigen in glaucoma patients.

In preferred embodiments of the method according to the invention algorithms using standard methods of multivariate statistical techniques, tree algorithms or artificial neural networks are used to calculate the transformation from a value of measured autoimmune reactivity to the corresponding glaucoma score according to step (d). Similarly, in step (e) algorithms are used in some preferred embodiments for the analysis of the determined glaucoma scores for each of the ocular antigens samples to determine the diagnostic result and in further preferred embodiments algorithms are used for both steps. In yet further variants the at least one glaucoma score of step d is the last step of the first method of diagnosis of glaucoma. According to these variants step e is not comprised by the first diagnostic method for glaucoma but is performed by a medical professional, who deducts a diagnostic result from the glaucoma scores.

A major advantage of the diagnostic method for glaucoma according to the invention is that the diagnostic result is based on the analysis of glaucoma scores of partially purified antigens of known identity.

In preferred embodiments a weight factor is assigned to at least one of the samples of ocular antigens. Such weight factors modulate the contribution of the autoimmune reactivity against a particular ocular antigen sample for the diagnostic result. In preferred embodiments the weight factor is calculationally introduced in step (c) or (d) or (e) of the first diagnostic method, however, in some preferred embodiments a weight factor is introduced in the steps (a) or (b) and in yet further embodiments weight factors are introduced in more than one of the steps (a)-(e). Weight factors have the effect to modulate the diagnostic result independently of the step at which they are introduced. A weighted glaucoma score results from a weight factor which has been introduced at any one or more than one of the steps (a)-(e).

According to preferred embodiments in which the diagnostic result is based on a weighted glaucoma score the specific weight factor is introduced in a computational step when the signals elicited from autoantibodies binding to individual antigens are detected and measured in a signal detection tool such as an optical reader.

According to further preferred embodiments the weight factor is introduced by differentially weighting the amount of individual antigens exposed to the reaction with autoimmune antibodies and/or by weighting one or more of the of analytical steps for detection and measurement of the autoimmune reactivity to individual antigens. Examples of such embodiments include detection of autoimmune reactivity with beads designed to be specific for different antigens and the weighting may be accomplished either by differential intensity of labeling of antigen specific beads or by a differentially graded sensitivity of the detector tool.

The glaucoma scores are for example weighted such that glaucoma scores for ocular antigen samples with a high diagnostic relevance are contributing more to the diagnostic result. In a simplified example, an ocular antigen sample X, which elicits autoimmune reactivities, which differ by a large significant value between glaucoma patients and healthy individuals, and with standard data from average values with low standard deviations, is generally of higher diagnostic relevance than an ocular antigen sample Y which elicits autoimmune reactivities differing only slightly between glaucoma patients and healthy individuals and are having average standard values with high standard deviation. Correspondingly and particularly, in a glaucoma test which is designed to maximize specificity, glaucoma scores for antigen sample X would be weighted more heavily than glaucoma scores for antigen sample Y to modulate their respective contribution to the diagnostic result.

It is a further advantage of the first diagnostic method, that the known partially purified ocular antigens, which are comprised in the samples of ocular antigens provided in step a) and/or any assigned weight factor can be chosen, is selected depending on the purpose of a particular diagnostic test for glaucoma. For example, in a screening test designed for diagnosis of glaucoma at an early stage of the disease, it would be desirable to maximize sensitivity. For such a diagnostic test application, a certain number of false positives are considered acceptable, but false negatives should be avoided.

A further advantage of preferred embodiments of the first diagnostic method is that from the knowledge about the physiological role of antigens, which yielded a high glaucoma score in a particular patient, additional diagnostic information can be extracted, thus enriching the diagnostic result.

As more and more is known how the progression of the disease correlates with autoimmune reactivity against ocular antigens, such antigens characteristic of a specific stage, particularly an early stage, may be used as biomarkers for monitoring the progression of the disease including monitoring the effectiveness of a medical treatment in slowing down or stopping the progression of the disease. Clinically, it is of great importance to identify among the individuals with an elevated intraocular pressure those, who develop glaucoma, in order to start treatment prior to the irreversible death of retinal ganglion cells.

In preferred embodiments of step a) of the method for diagnosis of glaucoma at least 2 partially purified ocular antigens, or at least 3 or 4 or 5 or 6 or 7 or 8 or 9 antigens or preferably at least 2 and less than 5 or 10 antigens of group 1 consisting of the following 48 ocular antigens are comprised in one or more samples of at least partially purified ocular antigens: actin, albumin, alpha-1-antitrypsin, annexin I-IV, annexin V, beta-2-adrenergic-receptor, brain derived neurotrophic factor (BDNF), calreticulin, cardiolipin, alpha-A-crystalline, alpha-B-crystalline, beta-L-crystalline, beta-S-crystalline, gamma-crystalline, DNA topoisomerase 1, fibronectin, α-fodrin (=spectrin), glial fibrillary acidic protein (GFAP), glutathion-S-Transferase, heat shock protein HSP10 (=chaperonin), HSP27, HSP60, HSP70, insulin, jo-1, lysozyme, myelin basic protein (MBP), myelin oligodrendrocyte glycoprotein (MOG), myoglobin, neuron specific enolase (NSE), neurotrophin 3, neurotrophin 4, neurotrophin 5, peroxide-dismutase, 3-phosphoserin, prealbumin, protein kinase C inhibitor, protein kinase C, superoxid dismutase, alpha-synuclein, gamma-synuclein, thyreoglobulin, transferrin, transthyretin, topoisomerase-inhibitor, ubiquitin, vascular endothelial growth factor (VEGF), vimentin.

The following subgroup of the above mentioned antigens, termed Group 2, have been identified as diagnostic markers for glaucoma for the first time. In further preferred embodiments of step a) of the method for diagnosis of glaucoma at least 1 partially purified ocular antigen, or at least 2 or 3 or 4 or 5 or 6 or 7 or 8 or 9 antigens or preferably at least 2 and less than 5 or 10 or 20 antigens of the following Group 2 consisting of 36 ocular antigens are comprised in one or more samples of at least partially purified ocular antigens: albumin, alpha-1-antitrypsin, annexin I-IV, annexin V, beta-2-adrenergic-receptor, brain derived neurotrophic factor (BDNF), calreticulin, cardiolipin, beta-L-crystalline, beta-S-crystalline, gamma-crystalline, DNA topoisomerase 1, fibronectin, heat shock protein HSP10 (=chaperonin), insulin, jo-1, lysozyme, myelin oligodrendrocyte glycoprotein (MOG), myoglobin, neurotrophin 3, neurotrophin 4, neurotrophin 5, peroxide-dismutase, 3-phosphoserin, pre-albumin, protein kinase C inhibitor, protein kinase C, superoxid dismutase, alpha-synuclein, gamma-synuclein, thyreoglobulin, transferrin, transthyretin, topoisomerase-inhibitor, ubiquitin, vascular endothelial growth factor (VEGF).

For some of the above mentioned group 1 antigens it has been previously known that autoantibody reactivities against them are different in glaucoma patients and healthy individuals. This has been confirmed (see examples and figures) and their autoantibody reactivity has diagnostic relevance for glaucoma also. These ocular antigens of group 3 are: actin, alpha-A-crystalline, alpha-B-crystalline, α-fodrin (=spectrin), glial fibrillary acidic protein (GFAP), glutathion-S-Transferase, HSP27, HSP60, HSP70, myelin basic protein (MBP), neuron specific enolase (NSE), vimentin.

The antigens of group 1 have been classified into the three subgroups A, B, and C. By methods described in the examples and figures, in which the autoimmune reactivities against different ocular antigens in healthy individuals and glaucoma patients are measured, the diagnostic relevance or the antigens has been evaluated. Antigens of group C or preferably antigens of group B or more preferably antigens of group A are comprised in the at least one sample of ocular antigens used for the first diagnostic method for glaucoma.

The following group of 24 partially purified ocular antigens has been identified as very highly relevant diagnostic markers for glaucoma and has been classified as group A antigens: actin, alpha-1-antitrypsin, annexin V, alpha-A-crystalline, alpha-B-crystalline, beta-L-crystalline, beta-S-crystalline, gamma-crystalline, α-fodrin (=spectrin), glial fibrillary acidic protein (GFAP), glutathion-S-Transferase, HSP27, HSP60, HSP70, jo-1, myelin basic protein (MBP), neuron specific enolase (NSE), protein kinase C inhibitor, superoxid dismutase, transferrin, transthyretin, ubiquitin, vascular endothelial growth factor (VEGF), vimentin. In preferred embodiments the at least one sample of ocular antigens provided in step a) comprises at least 2 antigens selected from Group A ocular antigens.

The following group of 9 partially purified ocular antigens has been identified as highly relevant diagnostic markers for glaucoma and has been classified as group B antigens: annexin I-IV, beta-2-adrenergic-receptor, calreticulin, heat shock protein HSP10 (=chaperonin), insulin, peroxide-dismutase, protein kinase C, alpha-synuclein, gamma-synuclein. In further preferred embodiments the at least one sample of ocular antigens provided in step a) comprises at least 2 antigens selected either from Group A and/or from Group B of ocular antigens.

Also the following group C of 14 partially purified ocular antigens has been identified as relevant diagnostic markers for glaucoma: albumin, brain derived neurotrophic factor (BDNF), cardiolipin, DNA topoisomerase 1, fibronectin, lysozyme, myelin oligodrendrocyte glycoprotein (MOG), myoglobin, neurotrophin 3, neurotrophin 4, neurotrophin 5, 3-phosphoserin, thyreoglobulin, topoisomerase-inhibitor.

In further preferred embodiments the at least one sample of at least partially purified ocular antigens comprises at least 1 antigen, or preferably at least 2 or 3 or 4 or 5 or 6 or 7 or 8 or 9 antigens or preferably at least 1 and less than 5 or 10 antigens or preferably at least 2 and less than 20 or all of the antigens, which belong to Group 2 or both Groups 2 and Group A classified as Group 2-A or which belong to Group 2 and either to Group A or to Group B classified as Group 2-AB.

A further aspect of the invention relates to an antigen carrying element carrying at least one sample comprising at least one at least partially purified ocular antigen. Preferred embodiments of the antigen carrying element include microarray chips, lateral flow test strips and microfluidic chips. In some preferred embodiments the antigen carrying element comprises a predetermined antigen zone which is a surface area on a strip or a slide or plate and the like or a predetermined surface in a device onto which the ocular antigen samples are spotted or microspotted. In yet other preferred embodiments the antigen carrying element additionally comprises a body fluid receiving zone. In further preferred embodiments the antigen carrying element comprises beads or another substrate which is coated with samples of ocular antigens. In further preferred embodiments the antigen carrying element carries weighted amounts of samples of ocular antigens and in yet further embodiments the antigen carrying element comprises ocular antigens selected from Group 1 or Group 2 or Group A or Group A and B or Group 2-A. It is certainly within the spirit of the invention to use combinations of the above mentioned features for the antigen carrying element according to the invention.

In a preferred embodiment of the first diagnostic method for glaucoma the element carrying the at least one sample of samples of ocular antigens is an antigen microarray chip. The at least one sample of ocular antigens is spotted as an antigen array or antigen microarray in a two-dimensional or three-dimensional matrix of spots on an antigen carrying element, which is for example a glass slide, a plate or a chip or a nitrocellulose slide or a hydrogel slide and the like. The protein arrays are prepared by spotting at least 2, preferably 3-5, or 3-9 or 3-12 samples of the at least partially purified ocular antigens of when applicable a particular group of antigens described above onto the carrier element such as onto a nitrocellulose-coated slides. The arrays are incubated with appropriately diluted samples of a body fluid such as blood serum, tears or aqueous humor. Autoimmune reactivity is detected e.g. by visualization of autoantibody-antigen-reactions on the arrays according to established techniques known in the art such as e.g. by treatment with a fluorescence labeled anti IgG antibody, followed by fluorescence scanning. The signals emitted from secondary antibodies are digitized; the spot intensities measured and optionally compared with results of body fluids from control individual using multivariate statistical techniques. Alternatives for the detection of autoantibody reactivity include visualization by anti-human IgG antibody coupled to an enzyme reacting with a component added or present on the antigen-carrying element resulting in the appearance of a color or in the change of a color. Such a change color in some applications may be visualized directly or by a detector tool such as an optical reader. In yet further preferred embodiments, autoimmune reactivities are measured with a competition assay, which is another established immunoassay technique: E.g. commercially available monoclonal fluorescent antibodies specific for certain ocular antigens are competing with autoantibodies, which are present in the body fluid of step b) for reacting with the least partially purified ocular antigens provided in step a). A strong autoimmune reactivity in the body fluid against a particular ocular antigen in such an assay results in a weak signal, because the fluorescently labeled commercial antibodies are hindered from binding to the antigens by unlabelled autoantibodies in the body fluid. Evidently, the invention is not limited to these examples of standard immunological assays known in the art which are mentioned here as mere examples, but extends to any standard immunological assay known in the art is applicable to determine the autoimmune reactivity in body fluids against at least partially purified ocular antigens.

In some preferred applications a weight factor assigned to individual antigens to modulate their contribution to the diagnostic result is introduced for example by spotting different amounts of antigen on the microarray, or by differential weighting of the signals elicited from antibodies bound to individual antigens. In further preferred embodiments the amounts of antigen spotted on the microarray are varied in order to modulate the expected signal intensity of the autoimmune reactivity such that it lies within the linear range of signal detection by the detector tool.

As further presented in example 7 a test for glaucoma with a selection with only 5 at least partially purified antigens results in a differentiation between glaucoma patients and healthy individuals with a specificity and sensitivity of approx. 90%. Thus, in further preferred embodiments the number of samples of ocular antigens is limited to a small number such as 10 or 8 or 6 or 5 or less than 5 in order to provide a test which is simple to analyze and which is producible at low cost, for mass screening of high numbers of individuals.

In a further preferred embodiment of the first diagnostic method for glaucoma, the element carrying the in the at least one sample of samples of ocular antigen is a lateral flow test strip. In preferred variants of these embodiments the antigen carrying element comprises a predetermined antigen carrying zone and a predetermined receiving zone for a body fluid. In further preferred variants the lateral flow strip optionally comprises several zones which comprise subzones. A selection of at least partially purified ocular antigens is applied to the antigen zone. Individual samples of ocular antigens may according to some variants of the method be applied to different subzones or mixed into one zone or several subzones. In a subsequent step a sample of body fluid which is optionally appropriately pre-treated and/or diluted, is applied to the receiving zone of the test strip. Appropriate reactants for visualization of autoantibodies, which are bound to antigens, may be included in the antigen zone or the receiving zone or both. Alternatively, the test strip with bound autoantibodies may subsequently to the binding step be incubated with reactants for visualization. Detection steps such as visualization are measured with or without analytical tools such as an image reader yielding a digitized output. In preferred applications a weight factor assigned to individual antigens for their contribution to the diagnostic result is introduced for example by applying different amounts of antigen to the antigen-zone of the test strip or by differential addition of chemical reactants or by differential weighting of the signals elicited from antibodies bound to individual antigens. Obviously, some of the features and combinations with features, which are described above for the embodiments of the method using microarrays are also equally applicable to preferred embodiments of lateral flow test strips.

Further preferred embodiments of lateral flow test strips are designed for directly contacting a patient with the receiving zone of the test strip to collect body fluid such as tears. Similar receiving zones for collecting body fluids are also part of other embodiments of antigen carrying element such as microfluidic chips or columns with antigen carrying beads comprising a receiving zone of adsorbent material.

It is known from the state of the art, that the absence of autoimmune reactivity or reduced autoimmune reactivity to certain antigens is also indicative of glaucoma. Therefore, some preferred embodiments are designed such that the absence or reduced binding of autoimmune antibodies to selected antigens is contributing to diagnostic result or is the basis for a diagnostic result. For example, in some embodiments of lateral flow test strips, one or more antigen subzones are spotted with antigens to which no autoimmunoreactivity is indicative of the disease, while other subzones are spotted with antigens which elicit a lower autoantibody reactivity in glaucoma patients than in healthy individuals, and/or with antigens which elicit a higher autoantibody reactivity in glaucoma patients than in healthy individuals and/or with antigens to which no autoimmunoreactivity is indicative of absence of glaucoma and favorable variations of the above combinations.

In a further preferred embodiment of the first diagnostic method for glaucoma the antigen carrying element for the in the at least one sample of antigens is a microfluidic chip or lab-on-a-chip device, wherein individual antigens are preferably provided in separate microchannels. The body fluid is loaded onto the microfluidic chip, or is received on a body fluid receiving zone of the chip. Subsequently, the body fluid is moved in to the microchannel system of the microfluidic chip for example by a pressure control unit. In preferred embodiments autoimmune reactivities are detected with secondary fluorescence labeled antibodies and standard optical readers or standard computers equipped with a camera and subsequently quantified and transformed into a glaucoma score as described. It is obviously within the spirit of the invention to combine features mentioned of other antigen carrying elements such as microarray chips and lateral flow test strips with features of microfluidic chips for further embodiments of antigen carrying elements for the methods and devices described in this application. This includes microfluidic chips with subzones for antigens with higher and other subzones for antigens with lower autoimmune reactivity in glaucoma patients versus healthy individuals.

Further aspects of the invention relate to test kits for the first diagnostic method for glaucoma and components of test kits comprising an element carrying a in the at least one sample of samples of ocular antigens and optionally auxiliary material. In some embodiments according to this aspect such a kit comprises antigen carrying elements carrying different variations of a in the at least one sample of samples of ocular antigens depending on the purpose of the diagnostic test. In some preferred embodiments of the kit the antigen carrying element comprises ocular antigens selected from Group 1 or Group 2 or Group A or Group A and B or Group 2-A, where in some of these preferred embodiments the amounts of antigens loaded on the antigen carrying element is weighted. In some preferred embodiments of the kit the antigen carrying element is or is part of a microarray slide, a lateral flow test strip or a microfluidic chip. In further embodiments of such test kits auxiliary materials such as analytical tools and or software is included for analytical tools such as an image reader and or software for an image reader yielding a digitized output of the test results of the test result is included, wherein this software is used for one or more of the steps of quantifying the measured autoimmune reactivity, calculating the glaucoma score or diagnostic result. In further preferred embodiments auxiliary material for taking a sample of body fluid is included. Such auxiliary material is for example blotting paper for receiving tears. Further preferred embodiments include reactants and/or reaction containers for detection and measurement of the autoimmune reactivity after incubation of the antigen carrying element with a body fluid or reactants for treating a body fluid sample prior to incubation with the antigen carrying element or for eluting the body fluid from an adsorbent material on which it was collected. Any combination of the above described features in the context of the methods for the diagnosis of glaucoma may be combined for further preferred embodiments of kits for performing the method for diagnosing glaucoma.

In further preferred embodiments of the first diagnostic method for glaucoma a body fluid specimen is first dried and then resolubilized or eluted prior to the reaction with the in the at least one sample of samples of ocular antigens. The body fluid specimen is collected either in a professional or a home setting. In some variants it is collected on a piece of adsorbent material such as a paper strip or directly in the receiving zone of the antigen carrying element or any receiving container for the body fluid. The body fluid specimen is allowed to dry and stored e.g. at room temperature. Experience shows that after storage for up to one week or also longer particularly at a lower temperature or if frozen, the autoantibodies present in the dried body fluid specimen can be reconstituted and eluted from the adsorbent material for example with a buffer or physiological saline solution. Thus, it is an advantage of this embodiment that collected body fluid specimen be collected for example by the patient herself at home and sent by mail to a laboratory for analysis. In further preferred embodiments of the first diagnostic method for glaucoma the body fluid, which is dried and reconstituted prior to analysis, is tears or blood serum.

In preferred embodiments of the first diagnostic method for glaucoma measuring the autoimmune reactivity in tears, the tears are collected with any standard method such as with pipettes or by a blotting paper strip such as a Schirmer paper strip or other suitable adsorbent material. Optionally, the tears are dried and stored e.g. at room temperature for up to one week or longer at 0-5° C. or longer when frozen.

Subsequently, the autoantibodies are eluted from the dried or still wet paper strip with buffer e.g. phosphate buffered saline. In further preferred embodiments the tears are directly collected onto a lateral flow test strip, e.g. by exposing the receiving zone of the test strip to tears in the eye. Obviously, one advantage of embodiments using tear fluid instead of e.g. blood serum is that samples of tears can be obtained non-invasively. This is a particular advantage for settings where no accordingly trained medical professionals are available such as in some ophthalmologist and optometrist offices as well as for self-testing.

A further aspect of the first diagnostic method for glaucoma relates to its use a rapid test for early detection of glaucoma prior to loss of vision in routine screening. Preferred embodiments are for example low cost diagnostic tests designed to be very sensitive such that in routine screening the likelihood of false-negatives is minimized. Accordingly, subsequent follow-up, more elaborate tests are e.g. relying on a larger number of ocular antigens and are designed to identify false-positives among those individuals with a positive test result in the rapid test. For example a lateral flow test strip, a microfluidic chip or a simple microarray chip as described in various embodiments above might be used for such rapid testing A further aspect of use of the first diagnostic method for glaucoma relates to its application for monitoring the progression of the disease and for monitoring the effect of medical treatment. In preferred embodiments of these aspects the selection of antigens and/or the weight factor assigned to them is designed to monitor autoimmune reactivity against antigens characteristic of a particular stage of the glaucoma disease.

A further aspect of the invention relates to a method of contacting a patient with a receiving zone of an antigen carrying element to collect a body fluid of the patient e.g. tears from the patient's eyes. In preferred embodiments the patient is contacted with a receiving zone of an antigen carrying element comprising adsorbent material wherein the receiving zone itself is free of antigen but the body fluid flows towards the antigen carrying zone. For example, a test strip with a receiving zone comprising adsorbent paper like a Schirmers' test strip is touched with the receiving zone to a human eye to collect tears. Subsequently, the tear fluid diffuses into the antigen zone and thus engages in step b of the method for diagnosis of glaucoma.

A further aspect of the invention concerns anyone of the of ocular antigens or any combination of one or more of the following group 2 of ocular antigens for the use in methods of diagnosing of glaucoma, or on an antigen carrying element for the use in methods of diagnosing glaucoma: albumin, alpha-1-antitrypsin, annexin I-IV, annexin V, beta-2-adrenergic-receptor, brain derived neurotrophic factor (BDNF), calreticulin, cardiolipin, beta-L-crystalline, beta-S-crystalline, gamma-crystalline, DNA topoisomerase 1, fibronectin, heat shock protein HSP10 (=chaperonin), insulin, jo-1, lysozyme, myelin oligodrendrocyte glycoprotein (MOG), myoglobin, neurotrophin 3, neurotrophin 4, neurotrophin 5, peroxide-dismutase, 3-phosphoserin, pre-albumin, protein kinase C inhibitor, protein kinase C, superoxid dismutase, alpha-synuclein, gamma-synuclein, thyreoglobulin, transferrin, transthyretin, topoisomerase-inhibitor, ubiquitin, vascular endothelial growth factor (VEGF).

A further aspect of the invention concerns anyone of the of ocular antigens or any combination of one or more of the following group 2 of ocular antigens or derivatives of ocular antigens such as fragments or modified ocular antigens or ligands such as antibodies, which are specific for anyone of the ocular antigens of group 2 for the use in methods of therapeutic treatment of glaucoma, or for the use in a composition for use in a medical treatment and specifically for use in a compositions for use in the treatment of glaucoma.

In preferred embodiments of using ocular antigens for a pharmaceutical composition to treat glaucoma, they are used as blocking agents binding to autoantibodies present at increased levels in a glaucoma patient. In particular, it has been found that many of the elevated autoimmune reactivities in glaucoma patients are directed against cytoskeletal proteins, for example actin and actin binding proteins such as annexin V, alpha fodrin, myelin basic protein, HSP 27. It is known that autoantibodies against cytoseleteal structures such as the f-actin meshwork when taken up by retinal ganglion cells disrupt the actin meshwork and induce cell apoptosis. Thus, according to this aspect of the invention, a pharmaceutical composition is provided, to prevent cell death of retinal ganglion cells. The composition comprising at least one of the ocular antigens of the group 2 stops the progression of glaucoma disease by ocular antigens, which bind to the autoantibodies and block their destructive effects on retinal ganglion cells in glaucoma patients.

While the first diagnostic method for glaucoma, which is independent of an elevated intraocular pressure, relies on a biomarker profile of identified ocular antigens, a second such diagnostic method which is independent of an elevated intraocular pressure relies on the effect of body fluids on a cell culture in an in vitro assay.

The second method for the diagnosis of glaucoma comprises the steps of a) providing an in vitro culture of cells; b) incubating a body fluid from a test individual with the in vitro culture of cells; c) analyzing expression of proteins by the in vitro culture of cells and/or analyzing viability of the cells after treatment according to step (b); and d) comparing the results of the analysis in step c) with standard data to determine a diagnostic result.

For step a) an in vitro culture of preferably human or animal primary or immortalized cells, more preferably mammalian cells are provided such as cells from a commercially available immortalized cell line. Preferably, neuronal cells and most preferably retinal ganglion cells or precursor cells of retinal ganglion cells are provided.

Protein expression patterns, expression of specific biomarker proteins and the viability of retinal ganglion cells exposed to body fluids from healthy individuals and patients with different forms of glaucoma or ocular hypertension can be differentiated. It is therefore a particular advantage of variable preferred embodiments of the method for the diagnosis of glaucoma that they differentiate between patients with different forms of glaucoma and furthermore among patients with ocular hypertension, those which have glaucoma or are at an elevated risk to develop glaucoma. Thus, this method, which is independent of monitoring ocular hypertension, renders possible early diagnosis of normal tension glaucoma and furthermore the differentiation between individuals affected by ocular hypertension which are suffering and which are not suffering from glaucoma.

In further preferred variants the body fluids or specimens or fractions thereof for the treatment in step b) are conserved e.g. by freezing and/or drying or by addition of a conservative such as conservatives found in commonly used serum tubes. After storage for a variable time period an adequately reconstituted sample of the body fluid is used for the treatment in step b) of the second diagnostic method.

In further preferred embodiments of the second diagnostic method, the body fluid is physically or chemically pretreated in order to stabilize or enhance their effect in step b) of the diagnostic test. For example, the body fluid may be partially purified to remove substances from the body fluid, which potentially interfere with the cell growth and protein expression of the cells in vitro cell culture provided in step a) in a manner unrelated to glaucoma or in order to show specific reactions of the cells provided in step a) to sub-fractions of the body fluid.

In further preferred variants of such embodiments the pre-treatment or fractionation yields a fraction of the body fluid, which comprises or is enriched with a predetermined selection of antibodies, such as antibodies or autoantibodies known to be specific for antigens associated with glaucoma or a certain form of the glaucoma disease. In further preferred variants at least one antibody is removed from the body fluid. In some of these variants, the removal of a selection of antibodies from the body fluid prior to its use in step b) serves to remove one or more antibodies, which inhibit cell growth or influence the protein expression of the cells in a way, which is not related to glaucoma and might obscure the diagnostic result. In further embodiments such removal serves the elimination of autoantibodies known to be specific for certain forms of glaucoma. In further preferred embodiments the cells are incubated with the removed antibodies in order to produce a reaction of the cell typical to the type of serum used.

The incubation of step b) is performed according to standard incubation techniques known in the art. In different variants of preferred embodiments of step b) the incubation time, incubation temperature and the level of applied hydrostatic pressure are varied.

In step c) the effect of the body fluid during incubation of step b) on the cells provided in step a) is analyzed. In a first group of preferred embodiments of step c) protein expression patterns are analyzed, in a second group of preferred embodiments of step c) expression of specific proteins such as biomarkers or antigens are analyzed, in a third group of preferred embodiments the viability of the cells is analyzed and in yet further preferred embodiments of step c) analysis by more than one of the above methods is performed. In all these embodiments of step c) the results of the analysis are used for step d) to determine a diagnostic result.

In preferred embodiments of the first group of preferred embodiments of step c), protein expression analysis is performed with entire proteins such as intact proteins as well as for example with digested or fractioned proteins obtained from the in vitro cell culture. For example, the whole range of the proteins in and on the cells as well as the extracellular proteins, in some variants including proteins, which the cells released into the medium. In preferred embodiments of step c) the proteins subjected to the protein expression analysis are obtained from the in vitro cell culture by cell lysis and recovered for example by precipitation, optionally pretreated for example by protein digestion, protein fractionation and/or separation and/or purification steps and analyzed by standard protein analysis techniques known in the art. Examples of applicable methods as known in the art include and are not limited to acetone precipitation, trypsin digestion, gel electrophoreses, HPLC etc.

In further preferred embodiments of the first group of preferred embodiments of step c) the protein expression analysis is performed by standard protein fingerprinting analysis known in the art such as mass spectroscopy, including MALDI-TOF TOF MS (matrix assisted laser desorption/ionisation time of flight mass spectroscopy), orbitrap mass spectroscopy, LC-MS (Liquid chromatography-mass spectrometry), HPLC-MS (high pressure liquid chromatography-mass spectrometry) and SELDI-TOF-MS (surface enhanced time of flight mass spectroscopy).

In further preferred embodiments of the first group of preferred embodiments of step c), the analysis the data of protein expression such as the protein expression patterns or fingerprints are processed by digital image analysis systems or other device for digitization as known in the art. In preferred embodiments digitized data are subsequently processed by multivariate statistical techniques, e.g. analysis of discriminance, classification/regression trees, and/or artificial neural networks.

In the second group of preferred embodiments of step c) expression of specific proteins are analyzed. In preferred variants of these embodiments the analysis of protein expression in step c) comprises an assay directed to at least one specific protein or biomarker. In preferred variants of such embodiments the biomarker is a protein known to be associated with the glaucoma disease or an autoimmune disease or a neurodegenerative disease or apoptosis. In preferred embodiments the assay for a biomarker is based on an immunoassay for example an immunoassay on the basis of chemiluminescence or fluorescence, as well as ELISA, Elispot or proteinarrays, which uses at least one antibody probe, which is preferably specific for such biomarkers known to be associated with the glaucoma disease or an autoimmune disease or a neurodegenerative disease or apoptosis. In preferred variants the antibodies are monoclonal antibodies.

In preferred embodiments of protein expression analysis using an immunoassay in step c) of the second diagnostic method, the antibodies which are used are specific antibodies against one or more of the 48 antigens of Group 1 disclosed in the first invention of this application. For all of these antigens it is known that their expression level is increased or decreased in glaucoma patients as compared to healthy individuals: actin, albumin, alpha-1-antitrypsin, annexin I-IV, annexin V, beta-2-adrenergic-receptor, brain derived neurotrophic factor BDNF, calreticulin, cardiolipin, alpha-A-crystalline, alpha-B-crystalline, beta-L-crystalline, beta-S-crystalline, gamma-crystalline, DNA topoisomerase 1, fibronectin, α-fodrin (=spectrin), glial fibrillary acidic protein GFAP, glutathion-S-Transferase, heat shock protein HSP10 (=chaperonin), HSP27, HSP60, HSP70, insulin, jo-1, lysozyme, myelin basic protein MBP, myelin oligodendrocyte glycoprotein MOG, myoglobin, neuron specific enolase NSE, neurotrophin 3, neurotrophin 4, neurotrophin 5, peroxide-dismutase, 3-phosphoserin, pre-albumin, protein kinase C inhibitor, protein kinase C, superoxid dismutase, alpha-synuclein, gamma-synuclein, thyreoglobulin, transferrin, transthyretin, topoisomerase-inhibitor, ubiquitin, vascular endothelial growth factor (VEGF), vimentin.

In further preferred embodiments of protein expression analysis with immunoassays in step c) of the second diagnostic method for glaucoma, the antibodies which are used are specific antibodies against one or more of the 36 antigens of Group 2 disclosed in the first invention of this application which are: albumin, alpha-1-antitrypsin, annexin I-IV, annexin V, beta-2-adrenergic-receptor, brain derived neurotrophic factor BDNF, calreticulin, cardiolipin, beta-L-crystalline, beta-S-crystalline, gamma-crystalline, DNA topoisomerase 1, fibronectin, heat shock protein HSP10 (=chaperonin), insulin, jo-1, lysozyme, myelin oligodendrocyte glycoprotein MOG, myoglobin, neurotrophin 3, neurotrophin 4, neurotrophin 5, peroxide-dismutase, 3-phosphoserin, pre-albumin, protein kinase C inhibitor, protein kinase C, superoxid dismutase, alpha-synuclein, gamma-synuclein, thyreoglobulin, transferrin, transthyretin, topoisomerase-inhibitor, ubiquitin, vascular endothelial growth factor (VEGF).

In further preferred embodiments of protein expression analysis with immunoassays in step c) of the second diagnostic method for glaucoma, the antibodies which are used are specific antibodies against one or more of the 24 antigens of Group A disclosed in the first invention of this application which are: actin, alpha-1-antitrypsin, annexin V, alpha-A-crystalline, alpha-B-crystalline, beta-L-crystalline, beta-S-crystalline, gamma-crystalline, α-fodrin (=spectrin), glial fibrillary acidic protein (GFAP), glutathion-S-Transferase, HSP27, HSP60, HSP70, jo-1, myelin basic protein (MBP), neuron specific enolase (NSE), protein kinase C inhibitor, superoxid dismutase, transferrin, transthyretin, ubiquitin, vascular endothelial growth factor (VEGF), vimentin.

In further preferred embodiments of protein expression analysis with immunoassays in step c) of the second diagnostic method for glaucoma, the antibodies which are used are specific antibodies against one or more of the 33 antigens of Group A or B disclosed in the first invention of this application which are: actin, alpha-1-antitrypsin, annexin V, alpha-A-crystalline, alpha-B-crystalline, beta-L-crystalline, beta-S-crystalline, gamma-crystalline, α-fodrin (=spectrin), glial fibrillary acidic protein (GFAP), glutathion-S-Transferase, HSP27, HSP60, HSP70, jo-1, myelin basic protein (MBP), neuron specific enolase (NSE), protein kinase C inhibitor, superoxid dismutase, transferrin, transthyretin, ubiquitin, vascular endothelial growth factor (VEGF), vimentin, annexin I-IV, beta-2-adrenergic-receptor, calreticulin, heat shock protein HSP10 (=chaperonin), insulin, peroxide-dismutase, protein kinase C, alpha-synuclein, gamma-synuclein.

In further preferred embodiments of protein expression analysis with immunoassays in step c), cells are lysed and for example the complete protein repertoire or specific protein fractions analyzed by Western Blotting or ELISA or ELISPOT or microarrays.

In preferred variants of embodiments comprising microarrays, antibodies, which may be monoclonal antibodies, or other capture agents for selected biomarkers, are deposited on a carrying element such as a chip surface including but not limited to a glass slide or a silicon or nitrocellulose surface and subsequently the chip is incubated with cell lysates or protein preparations obtained from cells after treatment according to step b). In other preferred variants, the element carrying the capture agents is a microfluidic chip or a test strip.

In further preferred embodiments, the protein expression analysis of step c) is performed in situ in the in vitro culture of cells. The in situ protein expression analysis includes, but is not limited to, labeling or label free methods as well as colorimetric methods such as fluorescence or chemiluminescence marking of intra- or extracellular proteins, application of the Elispot (Enzyme Linked Immuno Spot) method, measurement of changes in absorption through protein labeling in or on the cells as well as proteins in the medium etc. In situ protein expression analysis is preferably performed on the cells in the cell culture vessel after removal of the body fluid for step b).

In the third group of preferred embodiments of step c) the viability of the cells is analyzed. Analysis of cell viability includes but is not limited to cell counts e.g by flow cytometry and/or analysis of cell growth patterns, and/or monitoring viability and/or apoptosis and/or monitoring necrosis. Preferable methods include but are not limited to labeling the cells with annexin V and propidium iodide in order to detect necrosis and apoptosis as well as a WST-Test (water soluble tetrazolium) or alamar blue staining in order to detect the viability of the cells. In preferred embodiments results of different methods of analysis of viability are compared with standard data and combined for the determination of a diagnostic result according to step d). In further preferred embodiments, also results of the first and/or second group of preferred embodiments of step c) comprising protein expression analysis are combined with results of the third group of embodiments of step c) comprising analysis of cell viability.

In step d) the results of the protein expression analysis of cells and or cell viability analysis of step c) are compared with standard data to determine a diagnostic result. In preferred embodiments of step d) a calculative comparison of the protein expression of test cells with standard data is performed with computational methods known in the art.

In some preferred embodiments, the standard data used in step d) stem from control runs of the steps (a)-(c) of the method for diagnosis of glaucoma, which are conducted in parallel. The control runs include one or more and are not limited to the following samples: cells treated with a body fluid of glaucoma patients, including body fluids from glaucoma patients with specific known forms of glaucoma such as NTG (normal tension glaucoma) or POAG (primary open angle glaucoma) or of glaucoma patients at a specific stage of the disease, such as an early stage of the disease, and cells treated with a body fluid from healthy individuals. In other preferred embodiments such standard data may stem from stored data from control runs performed at a different time.

In the first group of preferred embodiments of step c) the diagnostic result determined in step d) differentiates between healthy individuals and glaucoma patients by protein expression analysis considering the complex protein profiles of proteins expressed by the cells analyzed of a test individual.

In the second group of preferred embodiments of step c), the diagnostic result determined in step d) differentiates between healthy individuals and glaucoma patients by protein expression analysis considering selected biomarkers among the proteins expressed by the cells after treatment with a body fluid according to step b).

In the third group of preferred embodiments of step c), the diagnostic result determined in step d) differentiates between healthy individuals and glaucoma patients by considering cell viability of cells after treatment with a body fluid according to step b).

In further preferred embodiments of the method according to the invention a computational processing step combines both processing of data from the results of the protein expression analysis and/or of the cell viability analysis in step c) and the comparison of the results of the protein expression analysis with standard data in step d).

In some preferred embodiments of step d), a calculative comparison of the results of the protein expression analysis and/or cell viability analysis of step c) is performed, which relies on computational methods known in the art. Patterns of highest similarity between the results of step c) of cells treated with a body fluid of a test individual in step b) and standard data corresponding to the results of step c) of cells treated in step b) with a body fluid from a control group such as variable clinical groups of patients or healthy individuals. In preferred variants the standard data are obtained from control runs performed in parallel in other variants the standard data stem from control runs performed at a different time.

In preferred variants of calculative comparison in step d) artificial neural networks are used, which learn to differentiate between different clinical groups from experience, not from programming. Examples of artificial neural network techniques applicable for step d) include multiple layer feed forward network (MLFN), artificial neural networks with self-propagation procedures, as well as other kinds of training algorithms, pruning techniques, and genetic algorithms.

The method of the invention not only includes the computational techniques as demonstrated herein for step d), but also similar technologies, e.g. the use of other pattern matching techniques, other classifying statistical techniques or other methods to compare the results protein expression with standard data—both for the comparison of complex protein expression profiles or the protein fraction profiles as well as for the comparison of the expression a limited number of biomarkers or antigens or the comparison of cell viability analysis.

The diagnostic result obtained by the first and second diagnostic method for glaucoma in some embodiments is diagnostic result ready to be understood by a patient or in other embodiments the diagnostic result comprises one or more diagnostic values to be interpreted by a medical professional.

BRIEF DESCRIPTION OF THE DRAWINGS

FIG. 2A: Coefficients of variability (CV) itemized for ocular antigens on study microarrays.

FIG. 2 B: Standard deviations (SD) itemized for different antigens on study microarrays.

FIG. 6: The receiver operating characteristic (ROC) curve for glaucoma detection by antibody reactivity for serum (6A) and for aqueous humor (6B). Receiver operating-characteristic for prospective serum samples (X-axis: 1-specificity, Y-axis: sensitivity, r=0.93)(6C).

FIG. 14: The graph shows the analysis of variance. FIG. 14a displays the influence of the various treatments of the cells—with serum of healthy individuals or POAG patients and ambient or elevated pressure—on the protein profiles of the cells. Obviously, the serum-type has a very large influence of 59.1% on the protein profile onto which another 14% can be added when combined with an elevated pressure (combination 1+2). The pressure itself has an 11.6% effect on the protein profiles of the cells. The graph in FIG. 14b shows the influence of the variance of the different treatments with respect to one selected specific biomarker: 9192. The effect is very similar.

FIG. 15a: showing an analysis of variance (ANOVA) calculating the influence of the presence of antibodies in the POAG serum on the protein profiles with 50.5%. The serum type, meaning POAG serum or serum from healthy controls, had an additional effect of 13.4%.

FIG. 15b: The Mahalanobis distances show the comparison of the overall protein profiles of the cells incubated with POAG serum either with or without antibodies to cells incubated with control serum where an increasing distance from point zero indicates an increasing difference in the protein profile of cells incubated with serum of POAG patients compared to the protein profile of cells incubated with healthy serum. The protein profiles of cells incubated with POAG serum differ significantly more from the protein profiles incubated with control serum as indicated by a Mahalanobis Distance of approx. 55 than the protein profiles of cells incubated with POAG serum from which antibodies have been removed (POAG—antibodies) as indicated by a Mahalonobis Distance of approx. 20.

FIG. 16a shows a fraction of the measured protein profiles from cells incubated with healthy, POAG or NTG serum in the presence or absence of pressure. The x-Axis shows the molecular weight of the proteins in Dalton and the y-Axis shows the measured intensity of the protein in the cells. It is obvious that the cells react differently to NTG serum in comparison to POAG serum.

FIG. 16b shows a biomarker at 9207 Dalton. The x-axis shows the experimental group and the y-axis shows the measured intensity of the protein in the sample. The glaucoma group includes all cells incubated with a glaucoma serum, thus with POAG or NTG serum. Clearly, the 9207 Dalton biomarker is up regulated in the cells incubated with glaucoma serum.

DETAILED DESCRIPTION OF THE INVENTION

Figure 1:
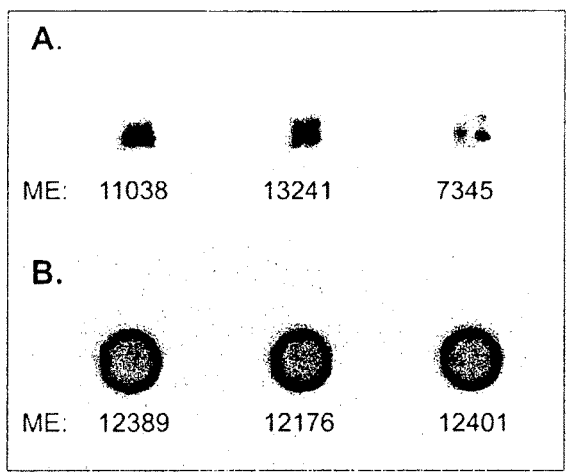
FIG. 1: Replicate spots of anti-human IgG/A/M generated by contact printing (A) and the piezo based spotting technique (B).

Examples and Detailed Description Concerning the First Diagnostic Method for Glaucoma

Example 1: Antigen Microarrays Comparing Autoimmunoreactivty in Sera and Aqueous Humor, with Characteristic Differences in Glaucoma Patients and Healthy Individuals Sera and aqueous humor of patients with primary open-angle glaucoma (POAG; n=13) and healthy controls (CTRL; n=13) were used for antibody analysis. The protein arrays were prepared by spotting 40-100 different purified antigens (known biomarkers) onto nitrocellulose-coated slides. The arrays were incubated with sera (1:250) and aqueous humor (1:20) respectively. For visualization of the antibody-antigen-reactions arrays were treated with a fluorescence labeled anti-human IgG antibody, followed by fluorescence scanning. The signals emitted from secondary antibodies were digitized and the spot intensities were compared using multivariate statistical techniques.

Results: The intraindividual comparison revealed congruencies but also differences between antibody patterns of sera and aqueous humor. In both, aqueous humor and serum, POAG patients showed more than twofold increased reactivities for α-1-Antitrypsin and Annexin V compared to healthy subjects ($P \leq 0.001$). In contrast, β-L-Crystallin showed a significantly increased mean (ME) reactivity in aqueous humor (POAG: ME=5049; SD=1638; CTRL: ME=2119; SD=673; $P \leq 0.01$) and a decreased reactivity in sera ($P \leq 0.01$) of POAG patients. For seven antigens none of the included study subjects showed immunoreactivity in aqueous humor. Using a biomarker panel of ten antibodies/antigens from each body fluid respectively, we were able to differentiate between POAG and CTRL with a specificity and sensitivity of approx. 90% (ROC-curve; serum: r=0.91; aqueous humor: r=0.93) using a special algorithm. These results confirm both up-regulations and down regulations of antibody reactivities in, sera and aqueous humor of glaucoma patients. Moreover, the increased reactivities in aqueous humor versus serum suggest a local antibody production in the eye.

Example 2: Procurement of Sera and Aqueous Humor Samples

Procurement of samples was performed in accordance with the Declaration of Helsinki on biomedical research involving human subjects. Blood and aqueous humor was collected from all volunteers giving their informed consent. The blood samples were centrifuged at 1000 g and the serum was stored at −80° C. for subsequent analysis. Aqueous humor samples were stored at −80° C. directly after sampling. All participants were subject of a full ophthalmologic examination, including Goldmann Applanation, Tonometry, optical coherence tomography (OCT) and Heidelberg retina Tomography (HRT), at the Department of Ophthalmology (University of Mainz, Germany) and they were classified in accordance with the guidelines of the European Glaucoma Society. 31 patients, undergoing cataract surgery, with a mean age of 73 (SD±10) and 37 primary open-angle glaucoma patients (POAG; mean age: 67, SD±10) were included in this study. Cataract patients with no clinical signs of primary or secondary glaucoma or other eye diseases than cataract, served as control group (CTRL) in accordance with other studies 42. POAG-patients had an IOP>21 mmHg without medication (determined by Goldmann Applanation Tonometry), typical visual field defects (examined by perimetry, OCTOPUS 101 Perimeter; Haag-Streit, Wedel, Germany) and optic nerve cupping. Patients with autoimmune diseases or suffering from neurologic diseases like Parkinson's disease were excluded from this study.

Example 3: Preparation of Microarrays

We used highly purified proteins, purchased at Sigma-Aldrich (Germany) and BioMol (Hamburg, Germany), as antigens. Antigens were diluted to 1 µg/µl with PBS buffer containing 1.5% Trehalose for optimal printing conditions. The spotting of antigens was performed with both a non contact printing technology (sciFLEXARRAYER S3, Scienion, Berlin, Germany), based on piezo dispensing, and the commonly used pin based contact printing technique (OmniGrid100, Digilab Genomic Solutions, Ann Arbor, USA). Results were comparatively evaluated for spot morphology and spot to spot variability. For printing of the whole set of study microarrays the piezo based spotting technique was used. Each antigen was spotted in triplicate onto nitrocellulose-slides (Oncyte, nitrocellulose 16 multi-pad slides, Grace Bio-Labs, Bend, USA). As a positive and negative control we used mouse anti human IgG/A/M (10 µg/µl) and spotting buffer. The spotting process was performed at RT and a humidity of 30%. 1 nl of each antigen-dilution was applied onto the nitrocellulose surface by spotting four times 250 pl on exactly the same position. The accurateness of the spotting volume and the correct positioning of the droplets were monitored prior and after the spotting process of each antigen using the sciDrop-VOLUME and autodrop-detection software (Scienion, Berlin, Germany).

Incubation and washing steps were performed at 4° C. on an orbital shaker (Titramax 100, Heidolph, Schwabach, Germany). Slides were covered with 16-pad FAST frame hybridization chambers (Whatmann, Maidstone, UK) and blocked with PBS containing 4% BSA for one hour. Afterwards slides were washed three times with PBS containing 0.5% Tween (PBS-T). Patient sera were diluted 1:250 in PBS and aqueous humor in a ratio of 1:10 in PBS. 120 µl of these dilutions were randomly incubated on prepared antigen-slides overnight. After several washing steps with PBS-T, slides were incubated with a fluorescent Cy-5 labeled secondary antibody (1:500 diluted in PBS-T, goat anti-human IgG, Jackson ImmunoResearch Laboratories, West Grove, USA) for one hour in the dark. Two washing steps with PBS-T were followed by two final washing steps with HPLC-grade water. All microarrays were air dried before scanning, using a microarray scanner (Affymetrix 428 TM Array Scanner, High Wycombe, UK). Generated 16-bit TIFF images (Tagged Information File Format) of slides were analyzed using the Spotfinder 3.1.1 software (TM4, Dana-Faber Cancer Institute, Boston, USA). Background substraction was performed according to the formula: spot intensity=mean intensitySP−((sumbkg−.sumtop5bkg)/(number of pixelSP−number of pixelstop5bkg)) where SP represents any spot, bkg the corresponding background and top5bkg the top five percent of background pixel. The coefficient of variance (CV) was calculated as follows: CV=SDSP3/meanSPX . . . SPn, where SDSP3 represents the standard deviation across three replicate spots of one antigen of one sample, and mean SPX . . . SPn the mean of all spot intensities.

Example 4: Statistical Analysis of Data

To provide skewing comparison of results caused by biases through data normalization and handling, we first contrast two different kinds of data transformation—area under the curve (AUC) and Z-score—with raw data. For analysis of study data, we applied Z-score transformation, according to the formula: Z-score=(intensitySP−mean intensitySP1 . . . SPX)/SDSPX . . . SPn, where SP represents any spot intensity and SP1 . . . SPX the overall intensity of all spots 46. Detection of potential biomarkers and estimation of significant changes in antibody reactivity was conducted by diverse statistical techniques. For intergroup comparison we used one-way ANOVA and multivariate analysis of discriminance (e.g. Mahalanobis distances, Canonical roots) for both sample materials separately. In the second step, artificial neural networks (ANN) were performed for determination of classification power of autoantibody patterns from a specific set of antigens. Therefore, data sets were randomly spitted in two parts with evened numbers of patients per group. One half was used for training of the ANN and the second half for testing the trained ANN regarding its classification power. So, no samples included into the training data set were used for classification purposes. Results were visualized by plotting sensitivity against specificity (ROC-curve). A detailed description of methods applied for statistical analysis could be found in previous publications of our group. For intraindividual comparison and in order to exemplify the proportion of aqueous humor antibody levels to those from corresponding sera samples we calculated the percental difference between both on basis of serum values for each single patient, followed by calculating the mean value over all subjects of the different patient-groups. Difference between sera and aqueous humor greater than 100% were considered as significant. Additionally, we correlated measured data with all collected clinical records. Statistical analyzes were conducted using Statistica 8.0 (Statsoft, Tulsa, Ariz., USA).

Example 5: GO Analysis

In order to get a deeper insight into biological processes of antigens with significant differences between patient-groups we used Cytoscape 2.6.2 in combination with the Bingo 2.3 plugin 50. To assign Gene Ontology (GO) annotations to each antigen, the full GO annotation database was utilized and for organism/annotation *Homo sapiens* was chosen. The hypergeometric model and the Benjamini & Hochberg False Discovery Rate correction ($P \leq 0.05$) assured significance of overrepresented protein functions.

Example 6: Scheme for an Exemplary Method of Determination of Glaucoma Scores

In a first step to determine glaucoma scores, the percentage difference between normalized intensity values of autoantibody reactivities of test samples and a reference sample are calculated. These percentage differences are used as input data for neural network analysis to determine a glaucoma score. Depending on the required sensitivity and specificity of the method for the diagnosis of glaucoma, the sera of step b) had been incubated with one of three exemplary options of samples: 1) or 2) or 3) which were provided according to step a) of the first diagnostic method: Sample 1) comprises all 48 at least partially purified ocular antigens of Group 1, sample 2) and sample 3) comprise 12 and 5 at least partially purified ocular antigens, respectively.

As expected, the larger the number of ocular antigens comprised by the sample according to step a), the better is the first diagnostic method with regard to sensitivity and specificity. In sample 3) with only 5 ocular antigens, still a sensitivity and specificity of approximately 90% was obtained.

Furthermore, individual antigens comprised in samples 1, 2 and 3 were assigned different weight factors for the glaucoma score calculation, such that highly weighted antigens (e.g. antigens of group A) have a higher impact on the glaucoma score.

Glaucoma scores differing from a defined reference value—e.g. exceeding a defined threshold value—identify those test samples, in which the body fluid was collected from a glaucoma patient.

Normalized intensity values
from autoantibody reactivities
⬇
Calculation of the percentage difference of intensity
values to reference values by the formula:

$$\% \text{ difference} = \frac{(\text{intensity value}_{patient} - \text{intensity value}_{reference}) * 100}{|\text{intensity value}_{reference}|}$$

Glaucoma scoring
Evaluation of a glaucoma score using neural network algorithm
with calculated percentage differences as data input:
1) Scoring based on all tested antigens
Sensitivity: 96%
Specificity: 97%
2) Scoring based on a subset of 12 tested antigens including:
MBP, GST, HSP27, protein kinase inhibitor C, GFAP, Jo-1, ubiquitin,
actin, beta-S-crystalline, HSP70, superoxide dismutase, transthyretin
Sensitivity: 92%
Specificity: 94%
3) Scoring based on a subset of 5 tested antigens including:
HSP70, actin, beta-S-crystalline, HSP27, GFAP
Sensitivity: 91%
Specificity: 88%
According to their impact on diagnosis of glaucoma and considering data from
statistical analysis such as post-hoc test or analysis of discriminance, antigens
are sub-divided into three different groups with different weights for the
calculation of the glaucoma score. Antigens showing a very strong inter-group -continued difference are assigned to group A, antigens with a strong difference are
assigned to group B and antigens with a distinct inter-group difference are
assigned to group C:
Group A (very highly relevant):
actin, alpha-1-antitrypsin, annexin V, alpha-A-crystalline, alpha-B-crystalline, beta-L-crystalline, beta-
S-crystalline, gamma-crystalline, α-fodrin (=spectrin), glial fibrillary acidic protein GFAP, glutathion-
S-Transferase, HSP27, HSP60, HSP70, Jo-1, myelin binding protein MBP, neuron specific enolase
NSE, protein kinase C inhibitor, superoxid dismutase, transferrin, transthyretin, ubiquitin, vascular
endothelial growth factor (VEGF), vimentin
Group B (highly relevant):
annexin 1-IV, beta-2-adrenergic-receptor, calreticulin, heat shock protein HSP10, insulin, peroxide-
dismutase, protein kinase C, alpha-synuclein, gamma-synuclein
Group C (relevant antigens):
albumin, brain derived neurotrophic factor BDNF, cardiolipin, DNA topoisomerase 1, fibronectin,
lysozyme, myelin oligodrendrocyte glycoprotein MOG, myoglobin, neurotrophin 3, neurotrophin 4,
neurotrophin 5, 3-phosphoserin, thyreoglobulin, topoisomerase-inhibitor
Antigens revealing a very high relevance for glaucoma diagnosis are stronger
weighted than antigens from group B or C, resulting in a higher impact on the
glaucoma score. Antigens with a high relevance are stronger weighted than
antigens from group C, resulting in a medium impact on the glaucoma score.
Relevant antigens got the smallest impact on the evaluated glaucoma score.
⇓
Subjects exceeding a defined treshold are diagnosed as glaucoma patient FIG. 1: Three replicate spots of anti-human IgG/A/M generated by contact printing (A) and the piezoelectric based spotting technique (B) are shown. Numbers represent the respective mean pixel intensities per spot. A: The mean intensity across all spots is 7173.32+/−1473.27 units. The coefficient of variability (CV) is 0.21. B: The mean intensity is 11716+/−374.78 units. The CV is 0.03. Two different spotting technologies were compared in order to find the best approach for the specific spotting of proteins with different physical characteristics in a reproducible way. A commonly used method to describe the variation of spot intensities across replicate spots is the determination of the coefficient of variance 45. Using the pin based contact printing technology we achieved a median CV of 0.32 across three technical replicate spots for all antigens. The spot morphology and intensity varies across the replicate spots, as shown in FIG. 1A. In contrast, microarrays spotted with the non-contact, piezo based spotting technique showed a more than 10 fold lesser spot to spot variability (median CV=0.029) and a much better constancy in spot morphology (FIG. 1B). These findings are consistent with data obtained from the sciDrop-VOLUME and autodrop-detection software. The software detected a drop-volume variation of just 0.8% (equivalent to 2 pl of a 250 pl droplet) across all antigens. Consequently, the non-contact printing technology was chosen for printing the whole set of study microarray slides in order to ensure the spotting of exactly equal volumes of antigen solutions. Similar to the estimation of the CV for the validation of spotting technologies we calculated the median coefficient of variance for technical replicate spots of the study microarrays. These microarrays exhibited a median CV of 0.031 with a standard deviation of 0.061 (for distribution of CVs for single antigens see FIG. 2.A), whereas the median standard deviation for measured intensities on replicate spots across all samples varies from 44 to 480, depending on the antigen and its averaged spot intensities (see FIG. 2.B).

FIG. 2 A and FIG. 2 B: FIG. 2 A depicts the coefficients of variability (CV) of raw data, itemized for each antigen on study microarrays. The x-axis represents the different antigens, the y-axis the CV values. The median CV across all antigens is 0.031+/−0.061. FIG. 2 B displays the standard deviations (SD) of raw data, itemized for different antigens on study microarrays. The x-axis represents the different antigens and the y-axis the values for the standard deviations (SD).

For antibody profiling of study patients and test individuals the comparison of different algorithm for data normalization revealed the Z-score transformation is most applicable to our approach, due to its low bias on ratios between study groups (FIG. 3) and the possibility to compare measurements in a quantitative manner across different experiments and glaucoma tests.

Figure 3:
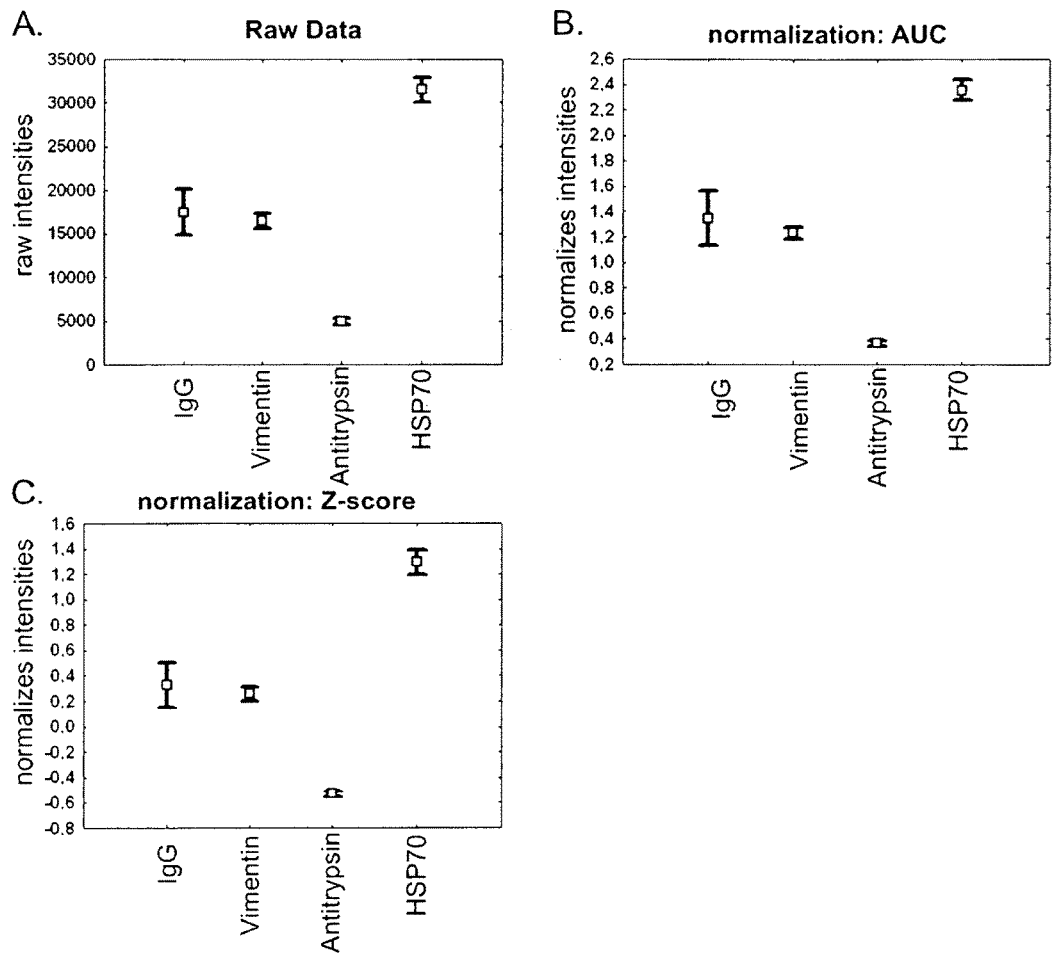
FIG. 3: Comparison of data obtained from different data handlings for four different antigens. Listed are: raw-data (A), AUC-data (B) and Z-score-data (C).

FIG. 3: Comparison of data obtained from different data handlings for four different antigens. Listed are: raw-data (A), AUC-data (B) and Z-score-data (C).

We could detect complex antibody reactivity patterns in all study patients and multiple differences between glaucoma patients and control subjects, in sera as well as in aqueous humor (FIGS. 4A and B). We found no correlation between the level of IgG/A/M and the age or the gender of patients, and we did not find significant differences in the IgG/A/M-levels of study groups, neither in sera (P≥0.9, FIG. 5 A) nor in aqueous humor (P≥0.6, FIG. 5B).

Figure 4:
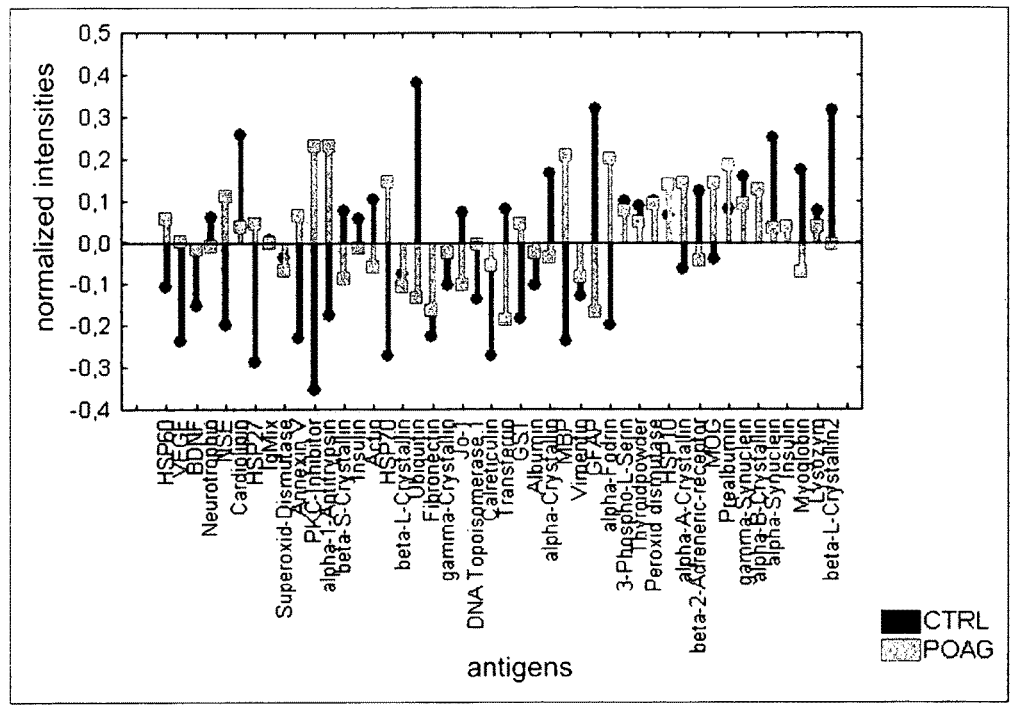
FIG. 4: Profiles of the averaged antigen intensities for 20 antigens incubated with serum (A) and aqueous humor (B) of control individuals (CTRL) and primary open angle glaucoma (POAG) patients.
Figure 4:
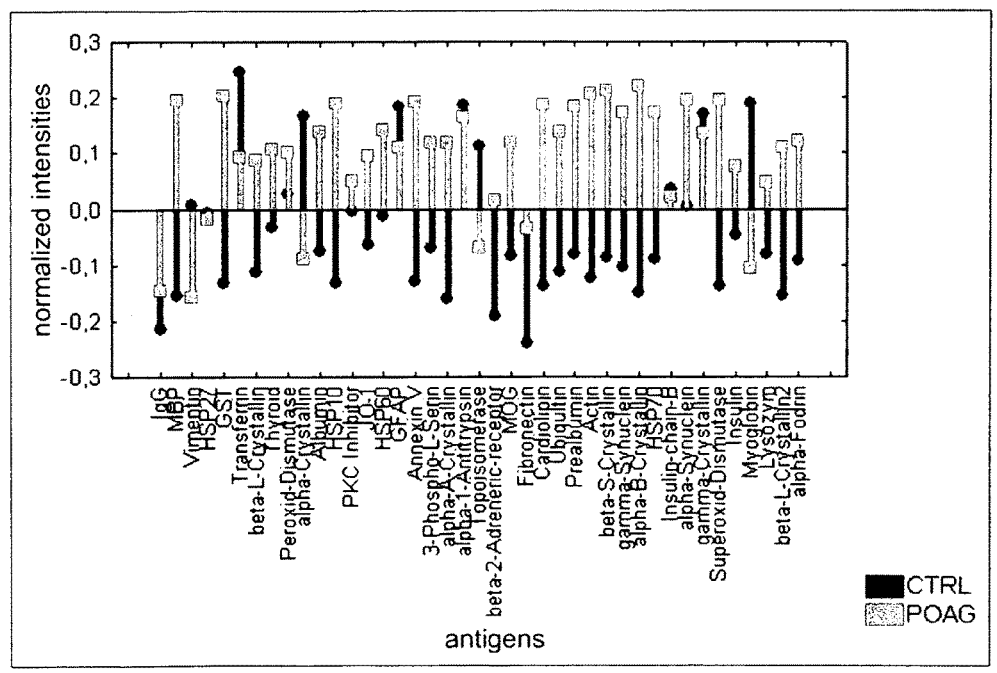

FIG. 4: Profiles of the averaged antibody intensities for serum (A) and aqueous humor (B). Shown are the averaged intensities of control subjects (CTRL) and primary open-angle glaucoma (POAG) patients, for 20 antigens. Line pattern represent patient groups (red=POAG, blue=CTRL), X-axis represents a subset of 20 antibodies which showed the strongest differences between groups, and the Y-axis depicts the value of computed Z-scores.

Figure 5:
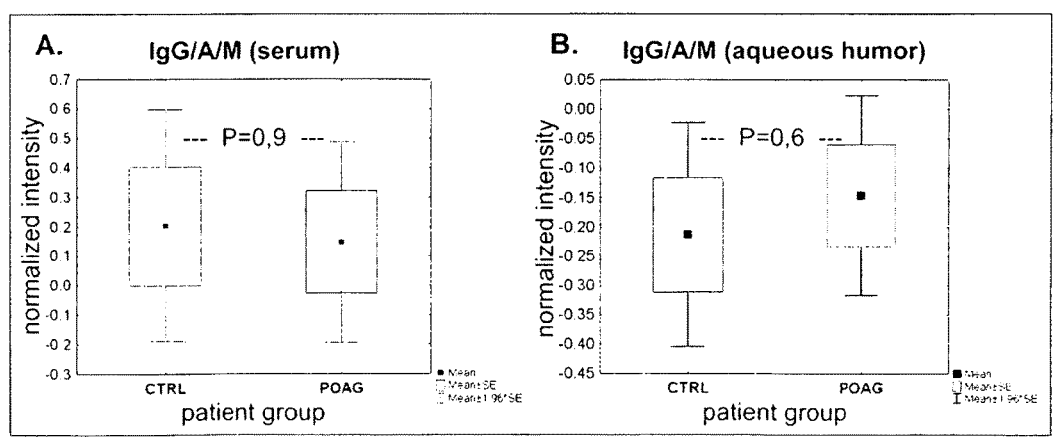
FIG. 5: Box-Plot for anti human IgG/A/M for healthy control individuals (CTRL) and glaucoma patients (POAG)

FIG. 5: Shown are the determined values for anti-human IgG/A/M as Box-Plot. The X-axis represents the different groups (control group (CON); glaucoma group (POAG)) and the y-axis the measured and normalized intensities (Z-score). No significant difference between both groups could be detected (P≥0.05) in sera (5A) or in aqueous humor (5B).

In sera, POAG patients showed several increased immunoreactivities in comparison to CTRL subjects, but revealed some decreased reactivities as well (FIG. 4A). As demonstrated, HSP27, HSP70, myelin basic protein (MBP) or Annexin V exhibited elevated antibody reactivities of POAG patients in comparison to the control group. For other antigens, such as the glial fibrilliary acidic protein (GFAP) or ubiquitin, POAG patients showed lower antibody reactivities than healthy subjects. Infrequent or very small, up to non-detectable, intensities were found for myoglobin, myelin oligodendrocyte glycoprotein (MOG) and DNA topoisomerase 1. The one-way ANOVA and the multivariate analysis of discriminance did not only reveal a significant difference between the whole antibody reactivities in sera of POAG patients and healthy controls (P≤0.002), but also a statistically significant difference for several single antigens. For example, POAG patients showed a significantly increased reactivity against MBP (P≤0.0028), HSP27 (P≤0.019), HSP70 (P≤0.0033) or α-fodrin (P≤0.0027) (table 3). Significantly decreased antibody reactivities were observed for GFAP (P≤0.001), ubiquitin (P≤0.0038) and β-L-crystallin (P≤0.03).

In the context of a potential utilization of autoantibody reactivities as a diagnostic tool for glaucoma, we tested their classification power by applying artificial neural networks (ANN). Training of the network was performed using a subset of patients (CTRL N=18, POAG N=17) and the data of the nine most significant serum antibody-antigen reactivities (14-3-3, Alpha-1-antitrypsin, beta-L-Crystallin, GFAP, HSP 27, HSP 70, MBP, alpha-fodrin, Ubiquitin). Subsequently, the trained network was applied to unknown serum samples. The personalized ANN output values for each patient, displaying the group classification through the ANN, were used as a combined antibody score (CTRL≥0.5, POAG≤0.5). Antibody scores calculated from samples of the serum training data set revealed a strong positive correlation with scores computed from aqueous humor samples of the same patients (R≤0.74, P≤0.001, FIG. 6A). Also, for prospective samples (CTRL N=13, POAG N=20; test data), not included into the training data set, we detected a correlation between serum and aqueous humor antibody-scores (R≤0.72, P≤0.001, FIG. 6B). Using the calculated antibody scores for patient classification only one subject (CTRL) was incorrectly classified as POAG subject by the serum and the aqueous humor antibody score (FIG. 6B). The strong positive correlation of the calculated scores from both sample types underlines the minor differences between serum and aqueous humor immunoreactivities detected via the intraindividual comparison. The sensitivity and specificity for a discrimination of prospective glaucoma and control subjects was 93% (FIG. 6C; AUC r=0.93).

FIG. 6: A, B: Scatterplots of serum and aqueous humor antibody reactivities. The X-axis shows values from serum antibody scores, the Y-axis values from aqueous humor samples. Each dot represents a single patient (blue dots=POAG, red dots=CTRL). A: Scatterplot for samples included into the training data set (R=0.74), B: scatterplot for all study samples (R=0.72). C: Receiver operating characteristic for prospective serum samples (X-axis: 1-specificity, Y-axis: sensitivity, r=0.93).

The examination of aqueous humor samples exhibit several differences between study groups, likewise (FIG. 4B). But unlike serum samples, only some few decreased reactivities appeared. Most of the antigens, like MBP, HSP70, annexin V or glutathione-S-transferase revealed increased reactivities for the POAG group, and several of these are in accordance with serum samples. For others, like insulin chain-B or MOG, infrequent antibody reactivities could be detected in aqueous humor and partly these are the same antigens which showed rare reactivities in serum (e.g. MOG or DNA topoisomerse 1, table 3.) Also, the statistical analysis fortifies the appearance of similarities between both sample types. Data thus obtained showed e.g. a P≤0.022 for MBP and a P≤0.03 for annexinV in aqueous humor—both antigens exhibit significantly increased values in sera of POAG patients, too. Coinciding with the lower number of univariate statistical significant differences between POAG and CTRL subjects, the ascertained classification power of aqueous humor samples was lesser (ROC-curve; AUC r=0.7) than the one of serum samples.

Figure 7:
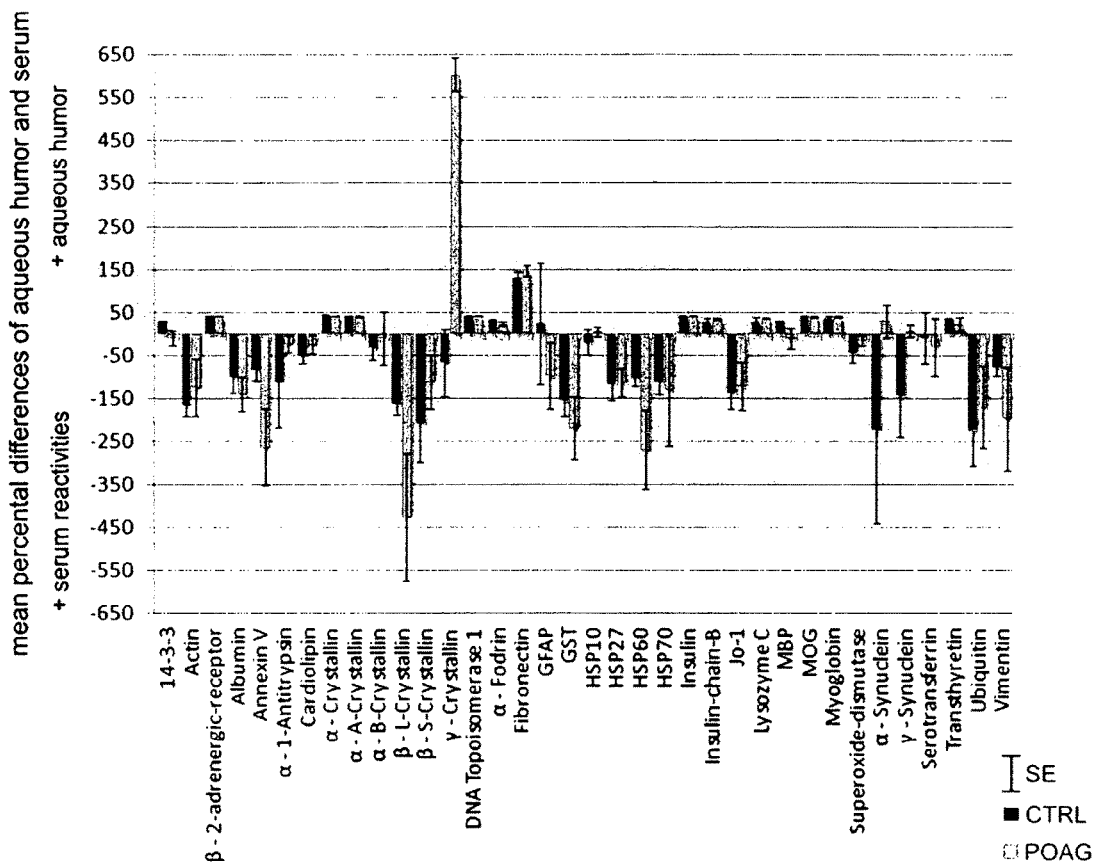
FIG. 7: Intraindividual comparison of serum and aqueous humor immunoreactivity values for the control group and POAG samples illustrated in FIG. 7.

FIG. 7: Intraindividual comparison of serum and aqueous humor immunoreactivities. Antigens are listed on the X-axis. The Y-axis represents the measured Z-score values. Bars above the zero line represent higher immunoreactivities in aqueous humor, bars beneath the zero line represent higher intensities in serum. Shown are the results for the control group and POAG samples as illustrated in FIG. 7. Overall, it can be observed that only few antigens show differences in immunoreactivities greater than 100% (=2 fold increase).

The intraindividual comparison of immunoreactivities from serum samples with those from corresponding aqueous humor samples revealed only some few significant differences. Regarding the CTRL subjects significant higher levels of serum antibody reactivities (e.g. MBP, HSP60, GFAP) could be observed, in comparison to corresponding aqueous humor samples, as well as significantly higher aqueous humor immunoreactivities (e.g. α-1-antitrypsin). But in its entirety, more than 80% of tested antigens revealed nearly similar immunoreactivities in sera and aqueous humor of control subjects. POAG patients revealed also some significant differences between sera and aqueous humor. For example, albumin and α-1-antitrypsin showed higher immunoreactivities in serum samples, and in the latter case this is contrary to control samples which showed a higher immunoreactivity for α-1-antitrypsin in aqueous humor. Aqueous humor samples from the glaucoma group revealed some higher antibody reactivities compared to corresponding serum samples as well (e.g. fibronectin, transthyretin). But as with the control group, only some few significant differences between serum and aqueous humor immunoreactivities appeared in the glaucoma group, and more than 80% of tested antigens revealed nearly congruent antibody patterns.

Figure 8:
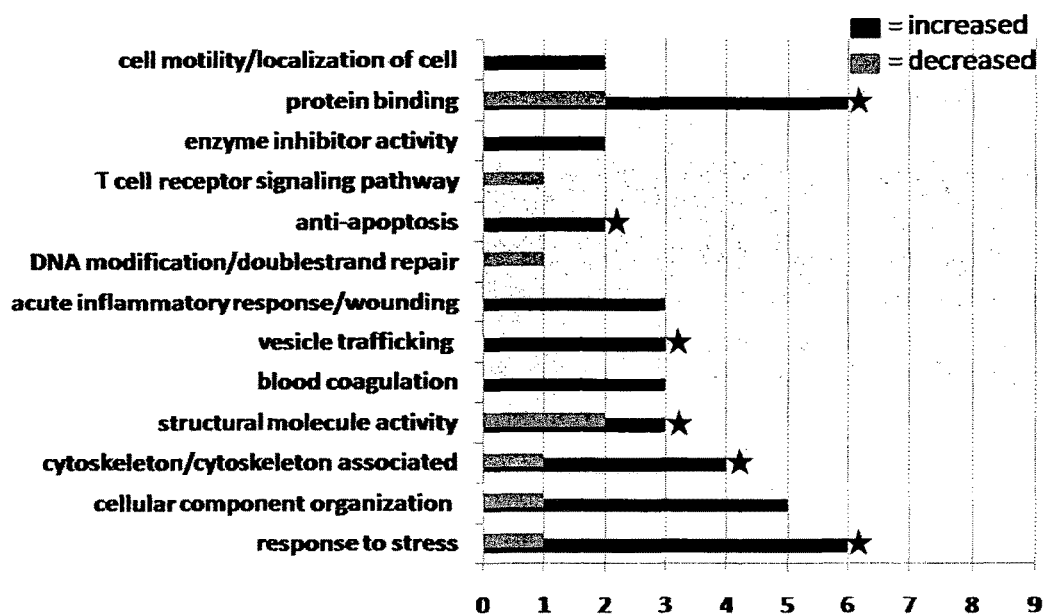
FIG. 8: Analysis of biological functions by GO annotations revealed several overrepresented terms by calculation trough the hypergeometric model for ocular antigens which showed significant differences between study groups in serum samples.

FIG. 8: Analysis of biological functions by GO annotations revealed several overrepresented terms. Calculation trough the hypergeometric model for antigens showed significant differences between study groups in serum samples. On the x-axis the numbers of proteins attributed to the different functional groups are shown.

Functional groups are listed on the y-axis. Blue bars represent antigens with a higher immunoreactivity in POAG subjects, red bars represent antigens with a lower immunoreactivity in glaucoma patients. Asterisk mark functional groups, which could also be found in aqueous humor.

Interestingly, terms like stress response, cytoskeleton, vesicular trafficking and apoptosis are significantly overrepresented (FIG. 8). Terms like cytoskeleton or vesicular trafficking are strongly connected to neurologic processes and others like stress response or apoptosis must be considered in conjunction with neurodegenerative diseases.

Figure 9:
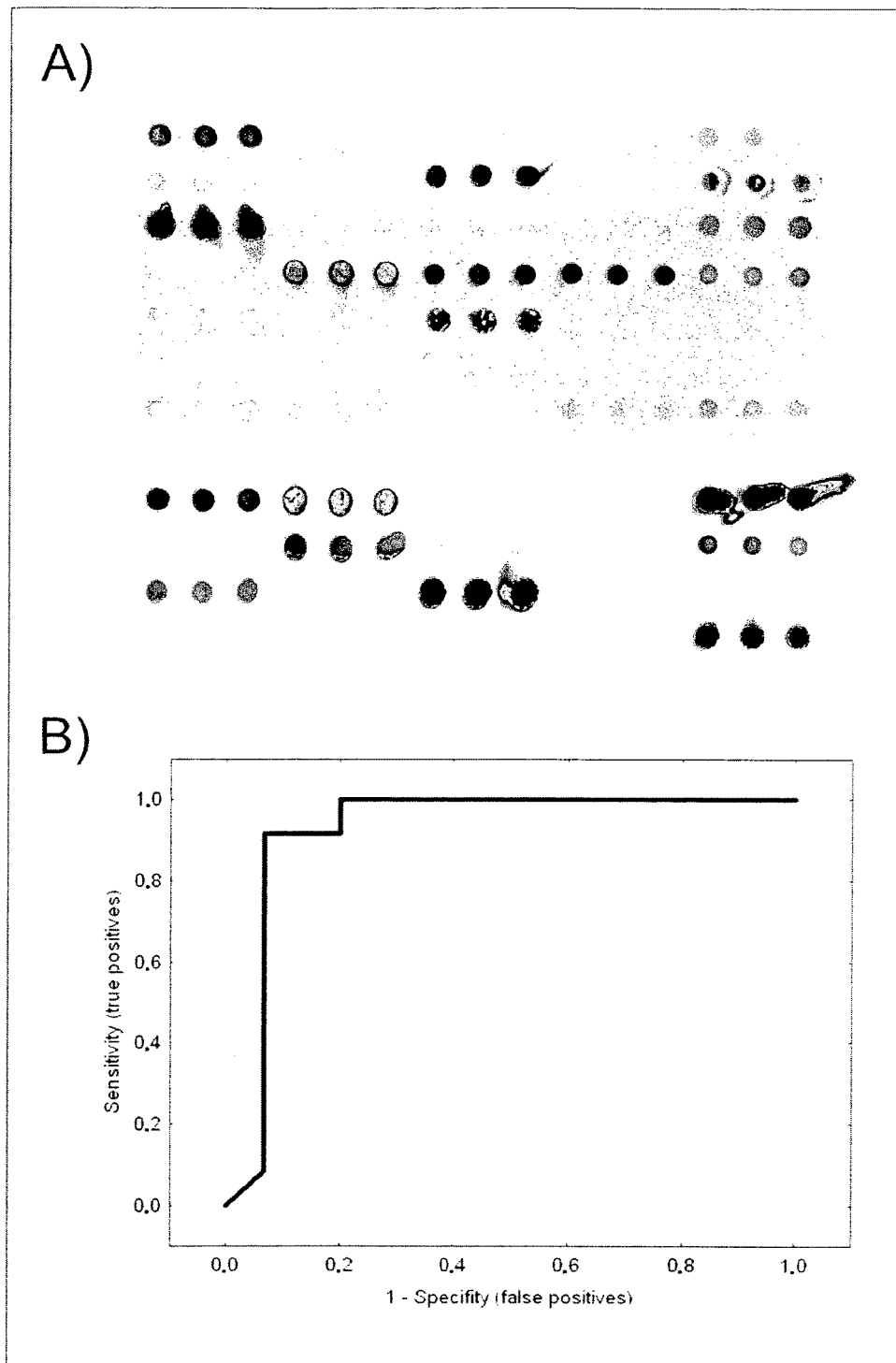
FIG. 9: Typical antibody pattern of a glaucoma patient.

FIG. 9: A: typical autoantibody pattern of a glaucoma patient. Tear proteins were eluted from a dried Schirmer strip fig. using phosphate buffered saline, followed by sample incubation on a protein microarray. B) Receiver operating characteristic curve (ROC curve). Tear autoantibody patterns from glaucoma patients and healthy subjects were used for training of an artificial neural network regarding pattern recognition of glaucoma patients. The y-axis represents the sensitivity and the x-axis the 1-specificity. Using these autoantibody patterns a specificity and sensitivity ≥90% could be achieved (area under curve: r=0.93).

Figure 10:
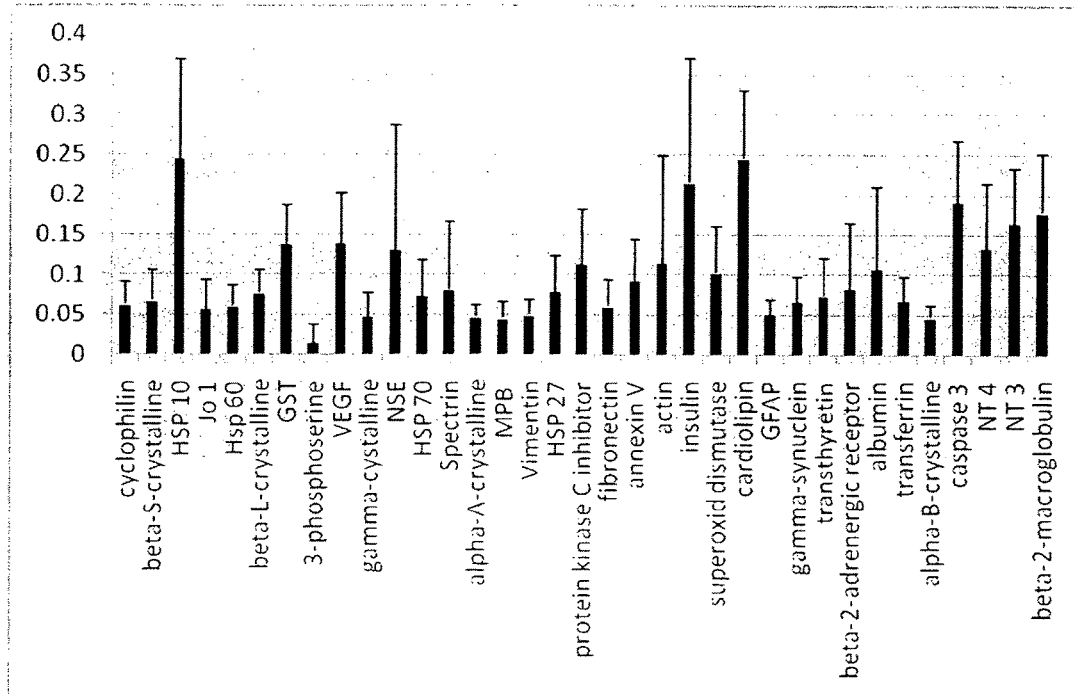
FIG. 10: Week to week reproducibility of microarray data

FIG. 10: Week to week variability of microarray data. A standard serum was incubated on seven consecutive weeks, followed by calculation of the coefficients of variance (CV). For several different antigens the CV (black bars) including standard deviation is depicted.

Using the protein-microarray approach we could confirm differences in antibody reactivities in sera and aqueous humor of glaucoma patients, as known in the art.

Furthermore, several new antigens, such as α-1-antitrypsin or annexin V, were found to have an impact in glaucoma. In comparison to control subjects we detected significantly increased immunoreactivities in sera and aqueous humor of POAG patients as well as significantly diminished reactivities in sera of glaucoma subjects. For several antigens, e.g. annexin V, chaperonin, HSP27, HSP60, HSP70 or MBP same kinds of differences between patient groups could be observed in aqueous humor and serum samples of glaucoma patients—giving a first hint for similarities between both sample types. In general, the differences between control subjects and glaucoma patients appeared to be less in aqueous humor samples, where only eight univariate significant differences between both groups could be detected, in contrast to eleven significant differences in serum samples. The intraindividual comparison of aqueous humor and sera revealed only some few antigens, e.g. MBP, GFAP or α-1-antitrypsin, to exhibit significantly different immunoreactivities between both sample types of control subjects. Also, in samples of glaucoma subjects few antigens, e.g. albumin or transthyretin, exhibit statistical significant differences between the immunoreactivity patterns of both body fluids. Compared to serum samples, transthyretin exhibited a higher autoantibody reactivity in aqueous humor of POAG patients, a result which is very interesting, considering the fact that higher amounts of transthyretin itself could be found in aqueous humor of POAG patients. In its entirety more than 80% of the antigen-antibody reactivities revealed to be congruent in both fluids, in healthy subjects as well as in POAG patients. This outcome indicates that immunoreactivities in an ocular fluid like aqueous humor, which is in close contact to the retina—the place of glaucoma pathogenesis—, are not that much different from systemic immunoreactivities in sera, in terms of antibodies. Thus, this finding underlines the specificity of detected changes in serum antibody patterns of glaucoma patients and may be important for other ocular diseases also.

Detailed Description and Examples Concerning the Second Diagnostic Method for Glaucoma:

According to preferred embodiments of the second method for detecting glaucoma for step a) a cell culture of the neuroretinal cell line R28 or the retinal precursor cell line RGC 5 was provided and in step b) the cells are treated under a normal or elevated pressure of 15000 Pascal (Pa) with serum from control individuals and from patients with primary open angle glaucoma (POAG), normal tension glaucoma (NTG) and ocular hypertension (OHT) patients. Ocular hypertension patients (OHT) have an intraocular pressure which is higher than normal in the absence of glaucoma symptoms such as optic nerve damage or visual field loss.

In the examples the following materials and methods were used. However, the invention is not limited to the combination of the materials and methods as described below and the methods described below may be substituted with alternative methods used for corresponding purposes.

Cell Culture:

The neuroretinal cell line R28 was used [provided from G M. Seigel; Ross Eye Institute, University of Buffalo]. This is a neuroretinal cell line derived from postnatal day 6 Sprague-Dawley rats and immortalized with 12S portion of E1A gene. The cell line shows characteristics of retinal precursor cells such as retinal ganglion cells, photoreceptor cell, Müller cells as well as glial cells [Seigel, G. M., A. L. Mutchler, and E. L. Imperato, Expression of glial markers in a retinal precursor cell line. Mol Vis, 1996. 2: p. 2]. Cultures were maintained in Dulbecco's modified Eagles Medium (DMEM) containing 10% Fetal Bovine Serum (FBS; Cambrex Bioscience, Verviers, Belgien), 5 mg/ml Gentamicine-Glutamine Solution (Sigma-Aldrich GmbH, Steinheim), 10% MEM Vitamins (100× (Invitrogen)) and 10% MEM non essential amino acids (100× (Invitrogen)). The cells were passaged every 4-5 days with a non enzymatic Cell Dissiciation Solution (Sigma-Aldrich GmbH, Steinheim) and grown in a humidified atmosphere of 95% air and 5% $CO_2$ at 37° C. The retinal precursor cell line RGC 5 [provided from N. Agarwal, UNT Health Science Center, Fort Worth] is a retinal cell line also immortalized with the 12S portion of the E1A gene expressing markers for neuronal cells as well as retinal cells [Krishnamoorthy, R. R., P. Agarwal, et al. (2001). "Characterization of a transformed rat retinal ganglion cell line." *Brain Res Mol Brain Res* 86 (1-2): 1-12; Van Bergen, N. J., J. P. Wood, et al. (2009). "Recharacterization of the RGC-5 retinal ganglion cell line." *Invest Ophthalmol Vis Sci* 50 (9): 4267-4272.]. Cultures were maintained in Dulbecco's modified Eagels Medium (DMEM) containing 10% FBS, 100 U/ml penicillin, 100 µg/ml streptomycin and 2 mM glutamine and grown in a humidified atmosphere at 37° C. with 5% $CO_2$. The medium was changed every second day and the cells were passaged every 4-5 days with a non enzymatic Cell Dissection Solution.

Preparation of Cell Lysates:

In some experiments the medium was discharged after 48 hours and the cells growing on the bottom of the 5 ml experimental plate were washed twice with 5 ml Phosphate buffered Saline (PBS; Invitrogen). 100 µl lysis buffer (Urea 9.5M, Chaps 2%, DTT 1%) with an added proteinase inhibitor mix (P 1860 (Sigma-Aldrich GmbH, Steinheim)) in a 400:1 proportion was pipetted on to the cells. These were then scrapped from the plate and given into an ice cooled Eppendorf tube. The cells were then lysed with an ultrasonic pulse echo instrument (Labsonic®M (Sartorius, Gottingen)) with an amplitude of 80% and frequency/Cycle of 0.5 for 3×25 times. After washing the cells in the 24 well-plates twice with 150 µl PBS, 60 µl of the Seldi buffer with the additional proteinase-inhibitor mix was added. The cells again were scrapped of the bottom of the well and lysed as mentioned above. The cells were put on ice after every lyses cycle with the ultrasonic pulse echo instrument. The protein concentration of the cell lysates from the 5 ml experimental well plates then were measured using the method of Lowry [Lowry, O. H., et al., Protein measurement with the Folin phenol reagent. J Biol Chem, 1951. 193 (1): p. 265-75].

In further experiments the medium was discharged and the cells washed with warm calcium free PBS. The cells then were detached from the cell culture plate using non enzymatic Cell Dissection Solution. The detached cells were centrifuged at 300 g for 10 min at 4° C. The supernatant was removed and the cell pellet washed with PBS. The cells were again centrifuged, the supernatant removed and the cells frozen at −80° C. After freezing the cells were thawn and lysis buffer with 0.1% Dodecyl D-β Maltosid and proteinase inhibitor was added. Cell lysis was enhanced by placing the cells with the lysis buffer into an ice cooled sonication bath for 1 min. The protein concentration was also measured using the method of Lowry.

Preparation of Total Proteins from Cell Lysates:

In order to measure the protein profiles of the cells an equivalent of 150 μg protein was removed from the cell lysates as prepared above and the proteins were precipitated with acetone by addition of 8 times the volume of acetone of −80° C. to the sample and incubated on ice for 30 minutes. The samples then were centrifuged at 14000 rpm at 4° C. for 30 minutes. The acetone then was discharged and PBS was added to the protein pellet leaving the end concentration of the proteins at 8 μg/μl. To dissolve the proteins in the PBS the tube was placed in an ultrasonic ice bath for 30 minutes. 2 μl of the sample then were spotted on the protein chips of the Seldi-Tof-MS.

Analysis of the Peptide Fragments by Orbitrap:

The equivalent of 60 μg protein was taken from the cell lysates prepared according to the method using Dodecyl-D-β-Maltosid and separated with a 12% Bis Tris gel electrophoresis (Invitrogen). The lanes were divided into 16 equally sized pieces and the proteins in these pieces were digested with trypsin. After digestion the proteins were extracted from the gel and the proteins of each piece were further fractionated into eight different fractions using C 18 ZipTips. The ZipTips were loaded with the samples and peptides were released from the Tip using an acetonitrile gradient from 10% to 50%. The fractions then were loaded onto an Orbitrap target and covered with a sinapinic acid matrix. The peptides were measured with the Orbitrap following the manufacturer's protocol. The information e.g. about the mass of the peptides gained by measuring the peptides with Orbitrap was sent to several databases and compared with known peptide fragments of proteins registered in the database. A list of measured proteins was generated. The intensity of the measured proteins in the different experimental groups was generated and compared.

Analysis of the Total Cell Proteins by Seldi-Tof-Massspectroscopy:

To analyze the protein profiles a surface-enhanced laser desorption/ionisation time-of-flight mass spectrometer PBS-II SELDI-TOF was used (commercially available at e.g. BioRad Hercules, Calif., USA or Ciperhgen Biosystems Inc Fremont). This mass spectrometer uses protein chips with different chemical surfaces. Each sample was loaded onto several eight spotted chips with either a weak cationic exchanger (CM10) or a reversed-phase surface (H50) [after treating these according to the manufacturer's protocol]. After letting the sample dry, 1 μl of sinapic acid-matrix, an energy absorbing molecule, (20 mg Sinapic acid, 750 μl ACN, 750 μl H2O-HPLC, 15 μl TFA) was pipetted on to every spot twice always allowing it to crystallize. The samples then were analyzed using a PBS-IIc Protein Chip Reader with a protein Chip Array Auto Loader which is able to analyze 24 chips at a time using the Protein Chip Software version 3.2. The samples were measured at a laser intensity of up to 200, a deflector setting of 2800 Da, a detector sensitivity of 9 and a molecular mass detection range of 3000-200000 Da., optimized from 3000-15000 Da.

Peak Detection of the Protein Profiles Measured by Seldi-Tof-MS:

The measured protein profiles then were sent to the Ciphergen Express Data Manager Software version 3.0 (CE; Ciphergen Biosystems). The baseline was subtracted and the peaks detected according to the manufactures protocol.

From the detected peaks a list of peak clusters for every experimental setup was generated. The cluster lists were exported to a statistical analysis program (Statistica, ver. 8.0; Statsoft, Tulsa, Okla.). The program was used to calculate a multivariate discriminant analysis based on combinations of multiple biomarker peaks. It can show which protein peaks are significantly different between the individual experimental groups and can be used to discriminate between the groups. In the first study comparing cells incubated with POAG serum to cells incubated with healthy serum a biomarker panel of 10 protein masses was detected which showed those peaks most capable of discrimination between the different groups.

Comparing the Results of the Protein Expression Analysis of Cells Incubated with Different Sera in the Presence or Absence of Elevated Pressure by Statistical Analysis:

Using statistics, a variance component and mixed model ANOVA was calculated in order to determine the influence of the dependant variables (serum-type/pressure-height) as well as of the independent variables on the protein profiles of the cells. The calculation was based on the canonical roots of the existing biomarker-panel. The influence of the variables also was calculated for every single protein biomarker. This analysis was also undertaken to calculate the influence of the antibodies in the serum on the protein-profiles. Also the Mahalanobis distances were calculated to show the direction the protein profiles changed after antibody removal.

Figure 17:
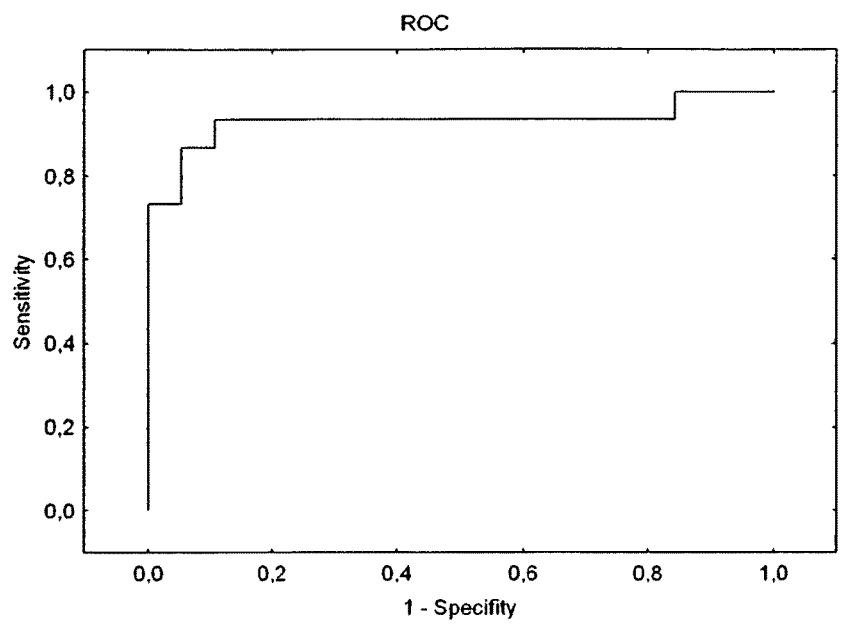
FIG. 17 shows a receiver operating characteristic (ROC) curve calculated on the basis of the measured protein profiles of the cells incubated with glaucoma serum, meaning POAG or NTG serum. It shows a distinction of a glaucoma serum from a non glaucoma serum with a sensitivity of 88% and a specificity of 90%. The area under the curve, which is a parameter for the accuracy of the test, is r: 0.92.

Using the calculated biomarkes a receiver operating curve (ROC) was calculated. It was able to document the detection of a glaucoma serum with a sensitivity of 88% and a specificity of 90%. The Area under the curve is r: 0.92 as shown in FIG. 17.

In addition a neural network was generated. This is a statistic data modeling tool that is fed with the peak information of the protein profiles. If the data is significant/potent enough the network has the ability to learn to differentiate between the experimental groups and is able to locate/associate new samples to the according group.

Protein Identification:

A Maldi-Tof-Tof MS was used to identify the protein-biomarkers measured with Seldi-Tof MS. The proteins in the cell lysates were separated via SDS-Page using an equivalent of 200 μg protein for every run after preparing them with an acetone precipitation. The remaining pellet was dissolved in 5 μl NuPage®LDS Sample buffer 4× (Invitrogen) diluted with 15 μl H2O. After denaturing the proteins at 90° C. for 5 mins they were separated with a 12% Bis-Tris Gel (Invitrogen) using NuPage®MES SDS Running Buffer 20× Invitrogen. After the run, the gels were incubated with a fixation solution (40 ml H2O, 50 ml Methanol, 10 ml acetic acid) for ten minutes followed by staining solution (Colloidal Blue staining kit, Invitrogen) (55 ml H2O, 20 ml Methanol, 20 ml Stainer A, 5 ml Stainer B) according to the manufacturers protocol over night. The proteins in the bands of the gel containing the biomarkers were eluted according to the following protocol: 2×1 mm parts of the band were cut from the gel and transferred into 100 μl Wash solution (Methanol 50%, H2O 40%, acetic acid 10%) and incubated for 30 minutes with vigorous shaking, subsequently dehydrated with 100% ACN for 20 minutes. Then 50 μl of the elution solution (formic acid 50%, ACN 25%, Isopropanol 15% H2O 10%) was added to the dried gel pieces and incubated for 4 hours. A 2 μl sample was measured with Seldi-Tof MS to show the eluted proteins. After showing the proteins with Seldi-MS, a digestion was undertaken. The rest of the band was cut into small pieces and 50 μl ACN was added for 15 minutes. After shot centrifugation and discharge of the ACN the gel pieces were dried with speed-Vac dryer for 10 minutes and covered with 50 μl Trypsin buffer (50 mM NH4HCO3, 14.8 ng/μl Trypsin) and left at 37° C. for approx. 12 h. 20 μl 25 mMNH4HCO3 was added to the digested proteins and subsequently the digested proteins were extracted by incubation for 30 minutes with 20 μl extracting solution (5% formic acid; 50% ACN; 45% H2O). Using the double layer method 1 μl of the digested proteins was loaded onto a MALDI ancor target using 2×0.5 μl cinnamic-acid matrix. The fractionized proteins were measured with a Maldi-TofTof MS (Bruker Ultra Flex II) according to the manufacturer's protocol.

Figure 11:
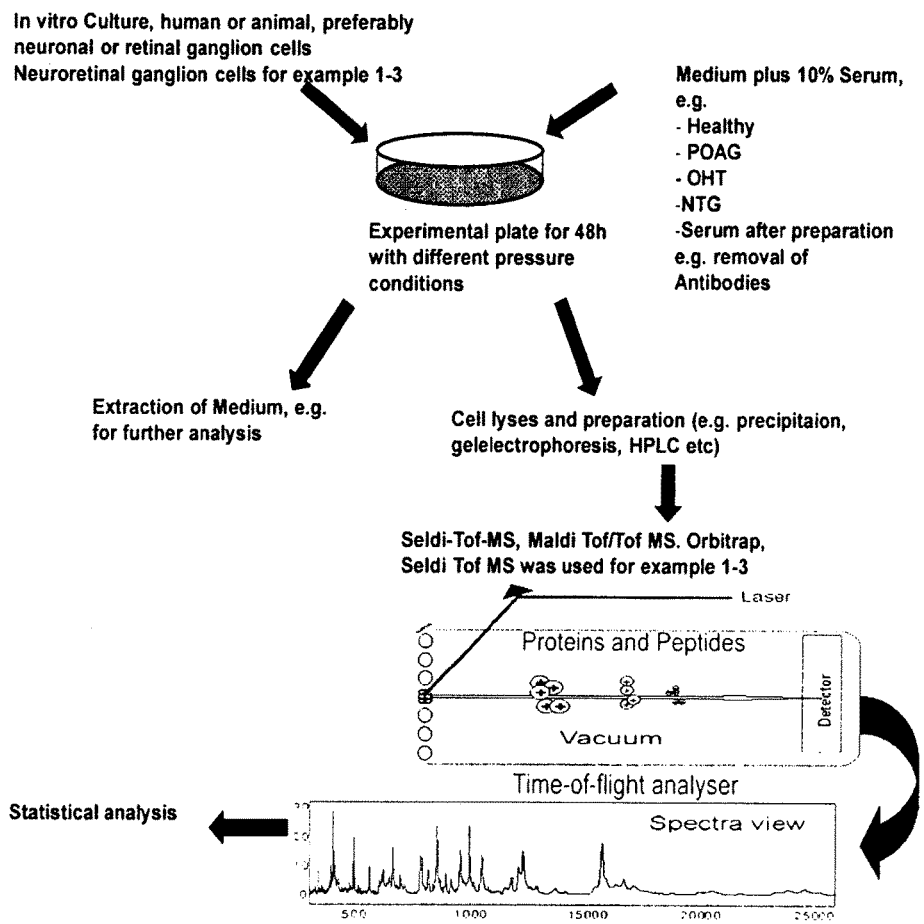
FIG. 11 gives a simple overview of the setup for a preferred embodiment of the second diagnostic method for glaucoma, which was used for examples 1-3: neuroretinal ganglion cells were plated in experimental plates and culture medium containing 10% serum from healthy individuals or patients with POAG (primary open angle glaucoma), NTG (normal tension glaucoma) or OHT (ocular hypertension) was added. The cells were incubated at 37° C. for 48 hours either at normal pressure or at an elevated pressure of 15000 Pascal. The cells were lysed and the proteins separated with an acetone precipitation. The protein profiles were measured with SELDI-TOF mass spectroscopy and then statistically analyzed.
Figure 12A:
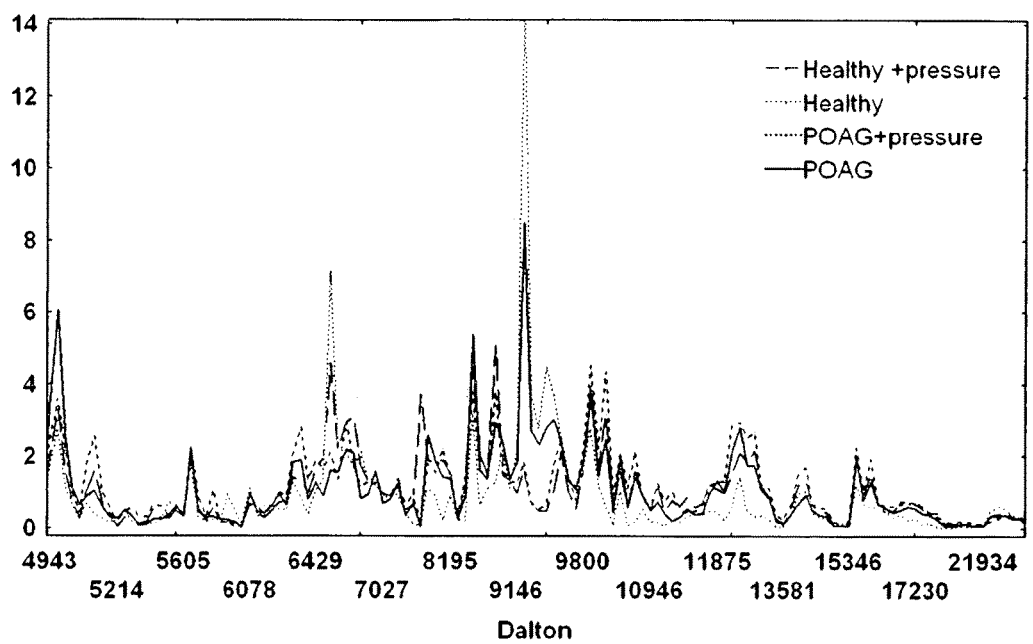
FIG. 12a shows a fraction of the measured protein profiles. The total protein profile counted approximately 400 different protein clusters. In the shown fraction the x-axis shows the molecular weight in Dalton and the y-Axis the intensity of the expression level of the protein in the cells. The very complex total protein profile measured by SELDI-TOF mass spectrometry protein clusters ranged from 3078 Dalton (Da) to 183222 Da. The fraction shown here ranges from 4943 Da to 21934 Da and gives an overview of the complexity of the proteins in the cells.
Figure 12:
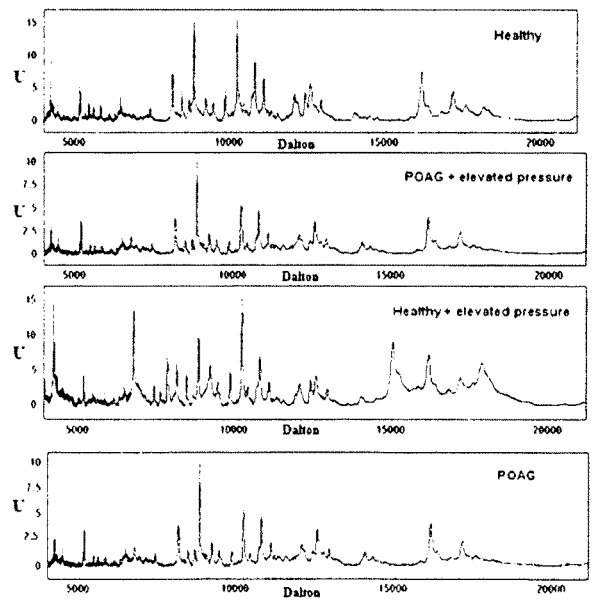
FIG. 12b shows several single measurements revealing the difficulty of identifying differences by mere visual analysis of the profiles. The sample profiles stem from cells treated with healthy or POAG serum with and without the presence of elevated pressure. The X-axis show the molecular weight of the proteins in Dalton, the Y Axis shows the intensity of the measured proteins in the cells. As the profiles show several hundred proteins it was not possible to analyze the differences between the experimental groups just by visually inspecting them.

The set up in examples 1-4 of the diagnostic test for glaucoma according to one preferred embodiment is outlined in FIG. 11. Example 1 was carried out in 5 ml (nunclon Surface) experimental plates according to the cell culture conditions described above. Examples 2 and 3 were carried out in 24 well plates and the cell culture conditions slightly adapted: The cells were plated in the plates with a confluence of ca 40% and treated with the DMEM-Medium as listed above containing 10% of the experimental Serum rather than FBS. They were then incubated in a humidified atmosphere of 95% air and 5% CO2 at 37° C. either with or without an elevated pressure of 15000 Pascal (112 mmHg) for 48 h. To generate an elevated [hydrostatic] pressure we used a specially designed glass pressure chamber. It was placed in an incubator at 37° C. and attached to a compressed air supplying device containing 95% synthetic air as well as 5% CO2 (AirLiquide, Ludwigshafen). The cells in example 4 were grown in 10 ml cell culture plates according to the cell culture conditions described above.

Example A

Example A was carried out in 5 ml (nunclon Surface) experimental plates. The protein profiles of cells incubated with healthy serum in the presence of either normal or elevated pressure were compared to protein profiles of cells incubated with serum from patients suffering from POAG. The number of samples in every group was n=8 using 4 different serum samples. The patients were classified according to the guidelines of the European Glaucoma Society (The European Glaucoma Society. Terminology and Guidelines for Glaucoma. http://www.eugs.org. 2004).

Figure 13:
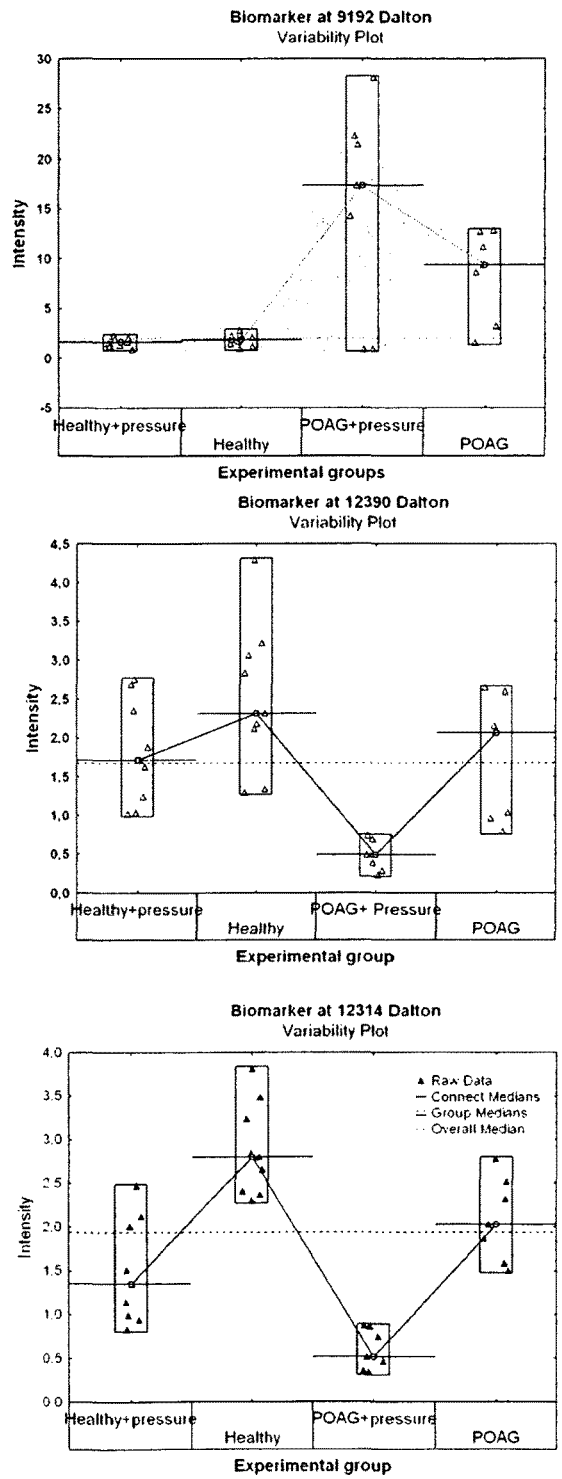
FIG. 13: shows several variability plots of the calculated biomarkers with the molecular weights of 9192, 12390 and 12314 Dalton. The x-axis represents the different treatment groups of the cells. The y-axis shows the intensity of the protein measured by SELDI TOF mass spectroscopy. Each triangle in a plot represents one sample of the specific group. The variability plots reveal that protein expression of these 3 biomarkers is altered (increased or decreased) in cells incubated with POAG serum as compared to cells incubated with healthy serum

Analysis of discriminance showed a panel of 10 proteins which were significantly up or down regulated in cells depending on the treatment of the cells prior to protein profile analysis: A: treatment with serum from healthy individuals and with pressure; B: treatment with serum from healthy individuals without pressure; C: treatment with serum from POAG patients and with pressure; D: treatment with serum from POAG patients without pressure. FIG. 13 shows three examples of protein-biomarkers with the molecular weights 9192, 12390, 12314 Da which all show significant differences in some of the groups. FIG. 13. shows the biomarker at 9192 Da (p=0.000058), which is up regulated in cells treated with serum from patients suffering from POAG both in the presence and absence of pressure. The biomarker at 12390 Dalton is significantly (p=0.000086) down-regulated only in those cells which were incubated with POAG serum and with an elevated pressure of 15000 pa as shown in FIG. 13. The analysis of discriminance also revealed biomarkers that were significantly (p=0.000000) down-regulated in those cells that were treated with pressure regardless to the type of serum. As example FIG. 13 shows the biomarker at 12314 Dalton.

FIG. 14a shows the contribution to differences in the protein profile by the various treatments A, B, C or D as described above. An analysis of variance was calculated looking at the overall influence of the serum-type, the pressure as well as the combination of both serum type and pressure on the protein profiles of the cells. FIG. 14 reveals that the serum-type had the greatest effect on the protein profiles namely 59.1%. The pressure itself had an effect of 11.6% on the protein profiles. Thus, the influence on the protein expression as evidenced by differences in the protein profiles is much greater by treating the cells with serum of POAG patients rather than serum of healthy individuals as compared to treating the cells with elevated pressure compared to ambient pressure.

The large influence of the serum type could not only be seen for the overall protein profile but also when calculating the analysis of variance for selected biomarkers. For example FIG. 14 b shows the analysis of variance for the biomarker at 9192 Dalton: Again the influence of the serum type is most important and it could be shown to have a significant effect of 55.1%.

These results from example 1 show that analysis of protein profiles of cells treated with serum of test individuals as compared to cells treated with serum from healthy individuals and/or POAG patients serves as a sensitive test for diagnosing POAG disease.

As described above, in preferred variants biomarkers or antigens are selected, of which it is known that their expression level is increased or decreased in glaucoma patients as compared to healthy individuals or in other autoimmune or neurodegenerative disorders or during apoptosis as compared to normal cell growth. An example for such a biomarker is the Histone H4: The protein at 9192 Dalton in Example A (FIG. 13) was identified by MALDI-TOF-TOF-MS as a fragment of the Histone H4 protein.

In example 1, the level of histone H4 expression, the 9192 Dalton biomarker—was significantly increased in those cells incubated with serum from patients suffering from glaucoma. This effect was increased by additionally incubating with an elevated pressure.

Histones H3 and H4 belong to the core histones, which assemble to nucleosome core particles of chromosomes in eukaryotic cells and are also involved in gene regulation. Histones, especially H3 and H4 can be posttranlationally modified e.g. by acetylation or methylation. Results of medical research have revealed that changes in the expression level, modifications and location of histones are associated with several other neurodegenerative diseases also, for example with Alzheimer disease and Parkinson's disease. Interestingly, histones not only play a role in the pathologic mechanism of several neurodegenerative diseases, but also in cancer cells, such as colon cancer cells, which are affected by changes in histone expression and modification. Considering the physiological role of histones, changes in the level of histone expression might well lead to apoptosis. This is in line with the fact that glaucoma is accompanied by apoptosis of retinal ganglion cells. Therefore, biomarkers or antigens known to be associated with the glaucoma disease—or also more generally which are known to be associated with an autoimmune disease or a neurodegenerative disease or apoptosis—are promising candidates for the protein expression analysis directed to selected biomarkers in step c).

Another interesting finding is, that during the 48 h of incubation with elevated pressure up to 35% of the cells, which were incubated with POAG serum lost their viability, whereas only roughly 10% of the cells, which were incubated with healthy serum, died.

Example B

Example B was carried out in 24 well plates. The protein profiles of cells incubated with healthy serum as a control were compared to protein profiles of cells incubated with serum from patients suffering from primary open angle glaucoma (POAG), normal tension glaucoma (NTG) and ocular hypertension (OHT) patients.

The protein profiles again showed a very complex pattern, FIG. 16 shows a magnified view of a range of the measured proteins. The analysis of discriminance again revealed a panel of significant biomarkers. Several of the biomarkers found in the first study with POAG serum could be found again in this experiment showing the same effect in terms of an up or down regulation as seen above. One of these biomarkers is at 9207 Dalton which can be looked at as the equivalent of the biomarker at 9192 Dalton found in the first experiment using only POAG serum and was increased in cells incubated with serum from glaucoma patients. The biomarker can be seen in FIG. 16b. As shown in previous examples the biomarker is up regulated in those cells incubated with glaucoma serum.

Example B yields another interesting result: Cells treated with sera of patients suffering from OHT have very similar protein expression profiles both for entire protein profiles as well as for selected biomarkers as cells treated with sera from healthy individuals. This result is in line with the clinical observation that only approximately 1% of the people with an elevated intraocular pressure develop glaucoma and the advantage of the method according to the invention is that this method is capable to identify those people with ocular hypertension who will develop glaucoma.

Example C

Example C was carried out in 24 well-plates. The protein profiles of cells incubated with healthy serum as a control were compared to protein profiles of cells incubated with serum from patients suffering from POAG either still containing the antibodies or after removal of the antibodies from the serum. The antibodies were removed using magnetic protein G beads (Dynabeads® Protein G; Dynal Biotech ASA, Oslo, Norway) which are coated with an affinity matrix for immunoglobulins. 20 µl beads were used to purify 35 µl serum. In order to use the beads they were washed twice with 600 µl NaAc, pH5, for 2 minutes and once for 5 minutes. The beads then could be added to the serum and incubated at 12° C. on an orbital shaker for 6 hours.

Analysis of variance for the changes in protein profiles of cells treated with serum from POAG patients and with serum from POAG patients from which antibodies have been removed as described above as compared to protein profiles of cells treated with serum from healthy individuals is displayed in FIG. 15. The influence of the antibodies on the protein profiles was as high as 50.5%. The calculation of Mahalanobis distances revealed that the protein profiles of those cells incubated with POAG serum after antibody removal changed significantly towards those cells incubated with healthy serum: The protein profiles of cells incubated with POAG serum differ from the protein profiles incubated with healthy serum more, as indicated by a Mahalonis Distance of approx. 55. The protein profiles of cells incubated with POAG serum from which antibodies have been removed (POAG—antibodies) differ from the protein profiles incubated with healthy serum less, as indicated by a Mahalonis Distance of approx. 20.

These results are in agreement with data presented in the first method for diagnosing glaucoma based on a difference in autoimmune reactivity in body fluids stemming from glaucoma patients versus healthy control individuals.

Example D

Example D was carried out in 10 ml cell culture dishes using RGC 5 cells which were incubated with POAG or healthy serum for a period of 24 hours. The protein or peptide pattern was measured with the Orbitrap. The cell lysates were also very complex and in a pilot study over 150 proteins were detected with the Orbitrap. After analyzing the differences in the intensity of the proteins measured by the Orbitrap we could detect significant differences between the experimental groups. We were able to detect proteins that were significantly up regulated in those cells incubated with healthy serum, e.g. Heat Shock Protein 60, Filamin B or Beta Actin, as well as proteins that were up regulated in those cells incubated with POAG serum, e.g. elongationsfactor 1 alpha, T-complex protein 1 subunit alpha B, Phosphoglycerate kinase 1.

| Protein | Healthy | POAG |
|---|---|---|
| Filamin-B (FLN-B) (Beta-filamin) (Actin-binding-like protein) (ABP-280-like protein)—(Mouse) | 16042 | 9315 |
| Actin, cytoplasmic 1 (Beta-actin)—(Mouse) | 28305 | 15835 |
| 60 kDa heat shock protein, mitochondrial precursor (Hsp60) (60 kDa chaperonin) (CPN60) (Heat shock protein 60) (HSP-60) (Mitochondrial matrix protein P1) (HSP-65)—(Mouse) | 16857 | 9368 |
| Elongation factor 1-alpha 1 (EF-1-alpha-1) (Elongation factor 1 A-1) (eEF1A-1) (Elongation factor Tu) (EF-Tu)—Mus musculus—(Mouse) | 12445 | 38739 |
| T-complex protein 1 subunit alpha B (TCP-1-alpha) (CCT-alpha) (Tailless complex polypeptide 1B) (TCP-1-B)—Mus musculus (Mouse) | 9592 | 20470 |
| Phosphoglycerate kinase 1 (EC 2.7.2.3)—Mus musculus (Mouse) | 12914 | 29310 |

Examples Concerning Therapeutical Applications of the Antibodies for Glaucoma

Example i

Figure 18:
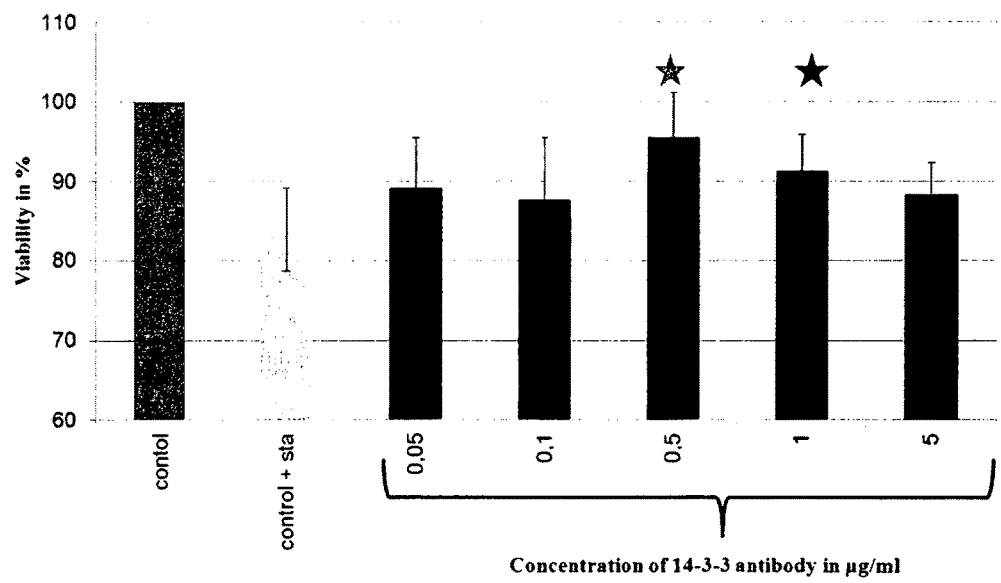
FIG. 18: shows the viability of RGC5 cells after incubation with different concentrations of 14-3-3 antibody and stress with 1.5 µM staurosporine (sta). The X axis shows the experimental group, the Y axis shows the viability of the cells in percent. The control cells (dark gray bar) show were incubated without cell stress or antibodies. The cells incubated with staurosporine show a loss of viability of 16.1%. Cells incubated with staurosporine and preincubated with 14-3-3 antibody show a significant ($p<0.05$) to highly significant ($p<0.01$) increase of viability in comparison to cells incubated with staurosporine of up to 11.6%. (antibody concentration 0.5 µg/ml).

RGC5 cells were plated in 24 Well plates with a number of 45000 cells per well. The cells were then preincubated with different concentrations of 14-3-3 (protein kinase c inhibitor) antibody for 3 h, known from to have a diagnostic potential (antibody from group 1) for glaucoma. In order to provoke cell stress and cell death the RGC5 cells were incubated with 1.5 µM staurosporine. After 5 h the viability of the cells was measured using crystal violet. We were able to detect a significant as well as highly significant increase of viability of stressed cells when incubated with different concentrations of 14-3-3 antibody. Significantly increased viability ($p<0.05$) of 7.4% could be detected for cells incubated with 1 µg/ml 14-3-3 antibody. A highly significant increase of viability (p<0.01) of 11.6% was detected in cells incubated with 0.5 µg/ml 14-3-3 antibody (FIG. 18).

Example ii

Figure 19:
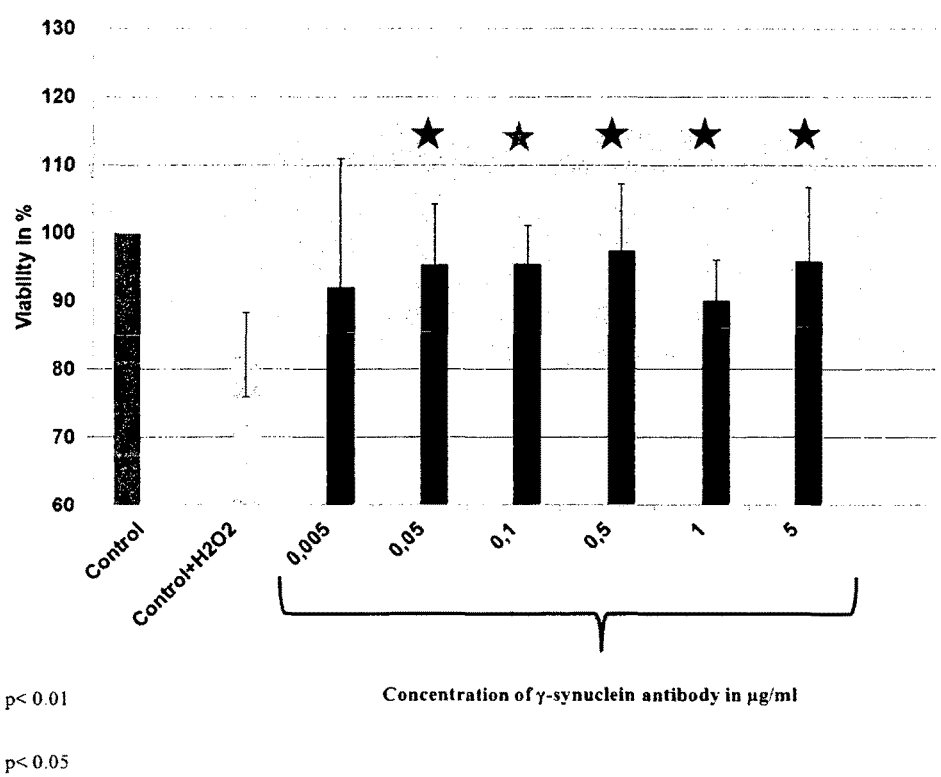
FIG. 19: shows the viability of RGC5 cells after incubation with different concentrations of γ-synuclein antibody and stress with 50 µM $H_2O_2$ (1 h). The X axis shows the experimental group, the Y axis shows the viability of the cells in percent. The control cells show were incubated without cell stress or antibodies. The cells incubated with $H_2O_2$ show a loss of viability of 17.9%. Cells incubated with $H_2O_2$ and preincubated with γ-synuclein antibody show a significant ($p<0.05$) to highly significant ($p<0.01$) increase of viability in comparison to cells incubated with $H_2O_2$ of up to 15.3%. (antibody concentration 0.05 µg/ml).

RGC5 cells were plated in 24 Well plates with a number of 45000 cells per well. The cells were then preincubated with different concentrations of γ-synuclein antibody for 3 h, known from to have a diagnostic potential (antibody from group 1) for glaucoma. In order to provoke cell stress and cell death the RGC5 cells were incubated with 50 µM $H_2O_2$. After 1 h the viability of the cells was measured using crystal violet. We were able to detect a significant as well as highly significant increase of viability of stressed cells when incubated with different concentrations of γ-synuclein antibody. Significantly increased viability (p<0.05) of up to 15.3% could be detected for cells incubated with different antibody concentrations (0.05; 0.5; 1 and 5 µg/ml) γ-synuclein antibody. A highly significant increase of viability (p<0.01) of 13.2% was detected in cells incubated with 1 µg/ml γ-synuclein antibody (FIG. 19).

Example iii

Figure 20:
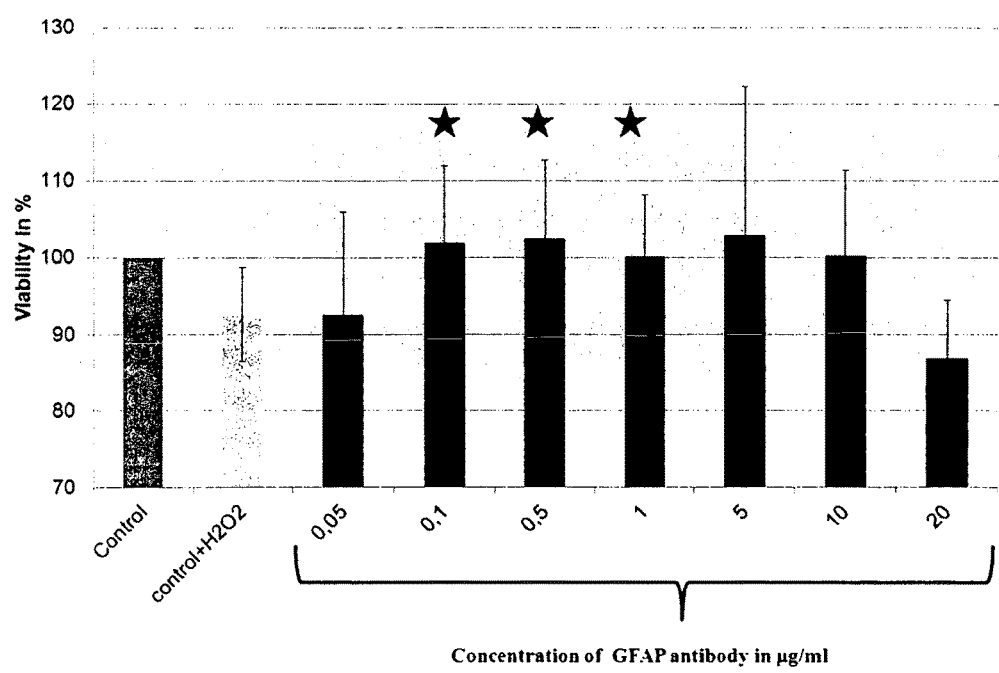
FIG. 20: shows the viability of RGC5 cells after incubation with different concentrations of GFAP antibody and stress with 50 µM $H_2O_2$ (1 h). The X axis shows the experimental group, the Y axis shows the viability of the cells in percent. The control cells show were incubated without cell stress or antibodies. The cells incubated with $H_2O_2$ show a loss of viability of 7.4%. Cells incubated with $H_2O_2$ and preincubated with GFAP antibody show a significant ($p<0.05$) increase of viability in comparison to cells incubated with $H_2O_2$ of up to 9.8%. (antibody concentration 0.5 µg/ml).

RGC5 cells were plated in 24 Well plates with a number of 45000 cells per well. The cells were then preincubated with different concentrations of GFAP antibody for 3 h, known from to have a diagnostic potential (antibody from group 1) for glaucoma. In order to provoke cell stress and cell death the RGC5 cells were incubated with 50 µM $H_2O_2$. After 1 h the viability of the cells was measured using crystal violet. We were able to detect a significant increase of viability of stressed cells when incubated with different concentrations of GFAP antibody. Significantly increased viability (p<0.05) of up to 9.8% could be detected for cells incubated with different antibody concentrations (0.1; 0.5 and 1 µg/ml) GFAP antibody (FIG. 20).

What is claimed is:

1. An assay device for assessment of glaucoma, comprising: (a) a solid support having one or more test antigen deposition locations; (b) a plurality of test antigens deposited and fixed on the solid support in the one or more test antigen deposition location in a dry state; wherein, the test antigens are purified test antigens purified to a level such that the test antigen or antigens affixed in any one test antigen deposition location constitute at least 70% of the total protein deposited in the test antigen deposition location; and the purified test antigens comprise HSP70, actin, beta-S-crystallin, HSP27 and GFAP, wherein the number of purified test antigens deposited and fixed on the solid support is 48 or less.

2. The assay device of claim 1, wherein purified test antigens further comprise myelin basic protein (MBP), glutathione-S-transferase, protein kinase C inhibitor, Jo-1, ubiquitin, superoxide dismutase and transthyretin.

3. The assay device of claim 1, wherein the purified test antigens consist of HSP70, actin, beta-S-crystallin, HSP27, GFAP, myelin basic protein (MBP), glutathione-S-transferase, protein kinase C inhibitor, Jo-1, ubiquitin, superoxide dismutase and transthyretin.

4. The assay device of claim 1, wherein the number of test antigens deposited and fixed on the solid support is 12 or less.

5. The assay device of claim 1, wherein the number of test antigens deposited and fixed on the solid support is 9 or less.

6. The assay device of claim 1, wherein one or more test antigens present in addition to HSP70, actin, beta-S-crystallin, HSP27 and GFAP, are selected from the group consisting of albumin, alpha-1-antitrypsin, annexin I-IV, annexin V, beta-2-adrenergic-receptor, brain derived neurotrophic factor (BDNF), calreticulin, cardiolipin, alpha-A-crystalline, alpha-B-crystalline, beta-L-crystalline, gamma-crystalline, DNA topoisomerase 1, fibronectin, α-fodrin (spectrin), glial fibrillary acidic protein (GFAP), glutathion-S-Transferase, heat shock protein HSP10 (chaperonin), HSP60, insulin, jo-1, lysozyme, myelin basic protein (MBP), myelin oligodrendrocyte glycoprotein (MOG), myoglobin, neuron specificenolase (NSE), neurotrophin 3, neurotrophin 4, neurotrophin 5, peroxide-dismutase, 3-phosphoserin, pre-albumin, protein kinase C inhibitor, protein kinase C, superoxide dismutase, alpha-synuclein, gamma-synuclein, thyreoglobulin, transferrin, transthyretin, topoisomerase-inhibitor, ubiquitin, vascular endothelial growth factor (VEGF), and vimentin.

7. The assay device of claim 1, further comprising a visualization reactant deposited on the solid support.

8. The assay device of claim 7, wherein the assay device is a lateral flow test strip.

9. The assay device of claim 8, wherein purified test antigens further comprise myelin basic protein (MBP), glutathione-S-transferase, protein kinase C inhibitor, Jo-1, ubiquitin, superoxide dismutase and transthyretin.

10. The assay device of claim 8, wherein the purified test antigens consist of HSP70, actin, beta-S-crystallin, HSP27, GFAP, myelin basic protein (MBP), glutathione-S-transferase, protein kinase C inhibitor, Jo-1, ubiquitin, superoxide dismutase and transthyretin.

11. The assay device of claim 8, wherein the number of test antigens deposited and fixed on the solid support is 10 or less.

12. The assay device of claim 8, wherein the number of test antigens deposited and fixed on the solid support is 9 or less.

13. The assay device of claim 1, wherein the device is a microfluidic device.

14. The assay device of claim 1, wherein the purified test antigens consist of HSP70, actin, beta-S-crystallin, HSP27 and GFAP.

15. A method of making an assay device for assessment of glaucoma comprising the step of depositing on a solid support a plurality of purified test antigens, wherein (a) the solid support has one or more test antigen deposition locations; (b) the two or more purified test antigens are deposited on the solid support in the one or more test antigen deposition location and fixed to the solid support when in a dry state; (c) said purified test antigens are purified from a test antigen preparation to a level such that the test antigen or antigens deposited and fixed in any one test antigen deposition location constitute at least 70% of the total protein deposited in the test antigen deposition location; and (d) the purified test antigens comprise HSP70, actin, beta-S-crystallin, HSP27 and GFAP, wherein the number of purified test antigens deposited and fixed on the solid support is 48 or less.

16. The method of claim 15, further comprising depositing a visualization reactant on the solid support.

17. The method of claim 15, wherein purified test antigens further comprise myelin basic protein (MBP), glutathione-S-transferase, protein kinase C inhibitor, Jo-1, ubiquitin, superoxide dismutase and transthyretin.

18. The method of claim 15, wherein the purified test antigens consist of HSP70, actin, beta-S-crystallin, HSP27, GFAP, myelin basic protein (MBP), glutathione-S-transferase, protein kinase C inhibitor, Jo-1, ubiquitin, superoxide dismutase and transthyretin.

19. The method of claim 15, wherein the number of test antigens deposited and fixed on the solid support is 10 or less.

20. The method of claim 15, wherein the number of test antigens deposited and fixed on the solid support is 9 or less.

21. The method of claim 15, wherein one or more test antigens present in addition to HSP70, actin, beta-S-crystallin, HSP27 and GFAP, are selected from the group consisting of albumin, alpha-1-antitrypsin, annexin I-IV, annexin V, beta-2-adrenergic-receptor, brain derived neurotrophic factor (BDNF), calreticulin, cardiolipin, alpha-A-crystalline, alpha-B-crystalline, beta-L-crystalline, gamma-crystalline, DNA topoisomerase 1, fibronectin, α-fodrin (spectrin), glial fibrillary acidic protein (GFAP), glutathion-S-Transferase, heat shock protein HSP10 (chaperonin), HSP60, insulin, jo-1, lysozyme, myelin basic protein (MBP), myelin oligodrendrocyte glycoprotein (MOG), myoglobin, neuron specificenolase (NSE), neurotrophin 3, neurotrophin 4, neurotrophin 5, peroxide-dismutase, 3-phosphoserin, pre-albumin, protein kinase C inhibitor, protein kinase C, superoxide dismutase, alpha-synuclein, gamma-synuclein, thyreoglobulin, transferrin, transthyretin, topoisomerase-inhibitor, ubiquitin, vascular endothelial growth factor (VEGF), and vimentin.

22. The method of claim 15, wherein the purified test antigens consist of HSP70, actin, beta-S-crystallin, HSP27 and GFAP.

* * * * *